US007968102B2

(12) United States Patent
Quentin-Millet

(10) Patent No.: US 7,968,102 B2
(45) Date of Patent: Jun. 28, 2011

(54) DENGUE CHIMERIC VIRUSES

(75) Inventor: Marie-Jose Quentin-Millet, Lyons (FR)

(73) Assignee: Sanofi Pasteur S.A., Lyons (FR)

( * ) Notice: Subject to any disclaimer, the term of this patent is extended or adjusted under 35 U.S.C. 154(b) by 1188 days.

(21) Appl. No.: 11/619,687

(22) Filed: Jan. 4, 2007

(65) Prior Publication Data

US 2010/0215692 A1     Aug. 26, 2010

Related U.S. Application Data

(60) Provisional application No. 60/863,708, filed on Jan. 13, 2006.

(51) Int. Cl.
*A61K 39/12*     (2006.01)
*A61K 39/295*     (2006.01)

(52) U.S. Cl. .................... 424/218.1; 424/202.1

(58) Field of Classification Search .................. None
See application file for complete search history.

(56) References Cited

U.S. PATENT DOCUMENTS 7,641,907 B2 *   1/2010   Kinney et al. .............. 424/218.1

FOREIGN PATENT DOCUMENTS

EP     1159968 A1 *   5/2000
WO    WO 93/06214 A1 *   4/1993

OTHER PUBLICATIONS

International Search Report for PCT/EP2007/050290 mailed May 7, 2007.
Butrapet et al., "Attenuation Markers of a Candidate Dengue Type 2 Vaccine Virus, Strain 16681 (PDK-53), are Defined by Mutations in the 5' Noncoding Region and Nonstructural Proteins 1 and 3," Journal of Virology, Apr. 2000, p. 3011-3019, vol. 74, No. 7, American Society for Microbiology.
Guirakhoo et al., "Recombinant Chimeric Yellow Fever-Dengue Type 2 Virus is Immunogenic and Protective in Nonhuman Primates," Journal of Virology, Jun. 2000, p. 5477-5485, vol. 74, No. 12, American Society for Microbiology.
International Preliminary Report on Patentability for PCT/EP2007/050290 issued Jul. 15, 2008.
Dunnen, et al., "Mutation Nomenclature Extensions And Suggestions To Describe Complex Mutations: A Discussion," Human Mutation, 2000, pp. 7-12; vol. 15, Wiley-Liss, Inc.
Freestone, D.S., "Yellow Fever Vaccine," Vaccines, 1995, pp. 741-779, second edition, W. B, Saunders, PA.

Gubler, D.J., "Dengue," The Arboviruses: Epidemiology and Ecology, 1988, pp. 223-260, vol. 2.
Gubler, D.J., et al., "Dengue and Dengue Hemorrhagic Fever," 1997, pp. 1-22, CABI International Publishing.
Huang Claire Y., et al., "Chimeric Dengue Type 2 (Vaccine Strain PDK-53)/Dengue Type 1 Virus as a Potential Candidate Dengue Type 1 Virus Vaccine," Journal of Virology, Apr. 2000, pp. 3020-3028, vol. 74, No. 7, American Society for Microbiology.
Kautner, Ingrid, et al., "Dengue Virus Infection: Epidemiology, Pathogenesis, Clinical Presentation, Diagnosis, and Prevention," Journal of Pediatrics, Oct. 1997, pp. 516-524, vol. 131, No. 4.
Peyrefitte, Christophe N., "Genetic Characterization of Newly Reintroduced Dengue Virus Type 3 in Martinique (French West Indies)," Journal of Clinical Microbiology, Nov. 2003, pp. 5195-5198, vol. 41, No. 11, American Society for Microbiology.
Pugachev Konstantin V., et al., "High Fidelity of Yellow Fever Virus RNA Polymerase," Journal of Virology, Jan. 2004, pp. 1032-1038, vol. 78, No. 2, American Society for Microbiology.
Rice, Charles M., et al., "Nucleotide Sequence Of Yellow Fever Virus: Implications For Flavivirus Gene Expression And Evolution," Science, Aug. 23, 1985, pp. 726-733, vol. 229.
Rigau-Pérez, Jose G., et al., "Dengue and Dengue Haemorrhagic Fever," The Lancet, Sep. 19, 1998, pp. 971-977, vol. 352.
Rothman Alan, et al., "Immunopathogenesis of Dengue Hemorrhagic Fever," Virology, 1999, pp. 1-6, vol. 257.
Sabin Albert B., "Research on Dengue During World War II," The American Journal of Tropicall Medicine and Hygiene, 1952, pp. 30-50, vol. 1, The Williams and Wilkins Company.
Smithburn, Kenneth C., et al., "Immunology of Yellow Fever,"Yellow Fever Vaccination, World Health Organization Monograph Series, 1956, pp. 1-238.
Vaughn, David W., et al., "Dengue in the Early Febrile Phase: Viremia And Antibody Response," Journal of Infectious Diseases, 1997, pp. 322-330, vol. 176, The University of Chicago.
Vaughn, David W., et al., "Dengue Viremia Titer, Antibody Response Pattern, And Virus Serotype Correlate With Disease Severity," Journal of Infectious Diseases, 2000, pp. 2-9, vol. 181, Infectious Diseases Society of American.
"WHO Technical Guide," Dengue Haemorrhagic Fever: Diagnosis, Treatment and Control, 1986, pp. 1-58, World Health Organization, Geneva.
Wu, Shuenn-Jue L., et al., "Human Skins Langerhans Cells Are Targets Of Dengue Virus Infection," Nature Medicine, Jul. 2000, pp. 816-820, vol. 6, No. 7.

* cited by examiner

*Primary Examiner* — Stacy B Chen
(74) *Attorney, Agent, or Firm* — McDonnell Boehnen Hulbert & Berghoff LLP

(57) ABSTRACT

The invention relates to Dengue chimeric viruses which are less prone to accumulate point mutations and genetic variations. In these Dengue chimeric viruses, the NS5 gene, which encodes polymerase, has been replaced by the corresponding NS5 sequence of a Yellow Fever virus.

9 Claims, 5 Drawing Sheets

DENGUE CHIMERIC VIRUSES

This application claims the benefit of priority of U.S. provisional application 60/863,708, filed Jan. 13, 2006.

BACKGROUND OF THE INVENTION

1. Field of the Invention

The invention relates to Dengue chimeric viruses of high genetic stability which are thus less prone to revert to a non-attenuated phenotype. In these dengue chimeric viruses, the NS5 sequence, which encodes polymerase, has been replaced by the corresponding NS5 sequence of a Yellow Fever virus.

2. Summary of the Related Art

Dengue disease is the second most important tropical infectious disease after malaria, with over half of the world's population (2.5 billion) living in areas at risk for epidemic transmission. An estimated 50 to 100 million cases of Dengue, 500,000 hospitalised DHF patients and 25,000 deaths occur each year. Dengue is endemic in Asia, the Pacific, Africa, Latin America, and the Caribbean.

Dengue haemorrhagic fever (DHF) is a severe febrile disease characterised by abnormalities of homeostasis and increased vascular permeability that can lead to hypovolemia and hypotension (Dengue shock syndrome, DSS) often complicated by severe internal bleeding. The case fatality rate of DHF can be as high as 10% without therapy, but below 1% in most centres with therapeutic experience (WHO Technical Guide, 1986).

Dengue diseases are caused by four closely related, but antigenically distinct, virus serologic types (Gubler, 1988; Kautner et al., 1997; Rigau-Pérez et al., 1998; Vaughn et al., 1997), of the genus Flavivirus (Gubler, 1988). Infection with a Dengue virus serotype can produce a spectrum of clinical illnesses ranging from a non-specific viral syndrome to severe, fatal haemorrhagic disease. The incubation period of Dengue fever (DF) after the mosquito bite averages 4 days (range 3-14 days). DF is characterised by biphasic fever, headache, pain in various parts of the body, prostration, rash, lymphadenopathy and leukopenia (Kautner et al., 1997; Rigau-Pérez et al., 1998). The viremic period is the same as of febrile illness (Vaughn et al., 1997). Recovery from DF is usually complete in 7 to 10 days but prolonged asthenia is common. Leukocytes and platelets counts decreases are frequent.

The viruses are maintained in a cycle that involves humans and *Aedes aegypti*, a domestic, day-biting mosquito that prefers to feed on humans. Human infection is initiated by the injection of virus during blood feeding by an infected *Aedes aegypti* mosquito. Salivary virus is deposited mainly in the extravascular tissues. The primary cell subset infected after inoculation is dendritic cells, which subsequently migrate to draining lymph nodes (Wu et al., 2000). After initial replication in the skin and draining lymph nodes, virus appears in the blood during the acute febrile phase, generally for 3 to 5 days.

Monocytes and macrophages are with dendritic cells among the primary target of dengue virus. Protection against homotypic reinfection is complete and probably lifelong, but cross-protection between dengue types lasts less than 12 weeks (Sabin, 1952). Consequently a subject can experience a second infection with a different serotype. A second dengue infection is a theoretical risk factor of developing severe dengue disease. However, DHF is multifactorial including: the strain of the virus involved, as well as the age, immune status, and genetic predisposition of the patient. Two factors play a major role in the occurrence of DHF: a rapid viral replication with high viremia (the severity of the disease being related to the level of viremia (Vaughn et al., 2000) and an important inflammatory response with release of high levels of inflammatory mediators (Rothman and Ennis, 1999).

There is no specific treatment against Dengue diseases. The management of DF is supportive with bed rest, control of fever and pain with antipyretics and analgesics, and adequate fluid intake. The treatment of DHF needs correction of fluid loss, replacement of coagulation factors, and infusion of heparin.

Preventive measures presently rely on vector control and personal protection measures, which are difficult to enforce and expensive. No vaccine against Dengue is currently registered. Since the 4 serotypes of dengue are circulating worldwide and since they are reported to be involved in cases of DHF, vaccination should ideally confer protection against all 4 dengue virus serotypes.

Live attenuated vaccines (LAVs), which reproduce natural immunity, have been used for the development of vaccines against many diseases. The advantages of live-attenuated virus vaccines are their capacity of replication and induction of both humoral and cellular immune responses. In addition, the immune response induced by a whole virion vaccine against the different components of the virus (structural and non-structural proteins) reproduced those induced by natural infection.

A dengue vaccine project was initiated in Thailand at the Centre for Vaccine Development, Institute of Sciences and Technology for Development Mahidol University. Candidate live-attenuated vaccines were successfully developed, at a laboratory scale, for dengue serotypes 1 to 4. These vaccines have been tested as monovalent (single serotype), bivalent (two serotypes), trivalent (three serotypes), and tetravalent (all four serotypes) vaccines in Thai volunteers. Those vaccines were found to be safe and immunogenic in children and in adults (Gubler, 1997). However, these LAV strains correspond to heterogeneous populations and represent a risk due to a potential in vitro or in vivo selection of one of the strain present in the composition. Indeed, dengue viruses are prone to generate mutations and genetic variations during their replication process.

Pugachev et al. (2004) have recently published that the polymerase encoded by the NS5 gene of the Yellow Fever virus is characterized by a greater fidelity as compared to other flaviviruses.

SUMMARY OF THE INVENTION

The inventors use the unique features of the Yellow Fever polymerase to construct chimeric recombinant Dengue viruses wherein the original polymerase encoding sequence is replaced by the corresponding sequence of a Yellow Fever strain thus leading to live attenuated dengue viruses of higher genetic stability which would represent useful vaccine candidates.

DETAILED DESCRIPTION OF THE INVENTION

Definitions

Figure 1:
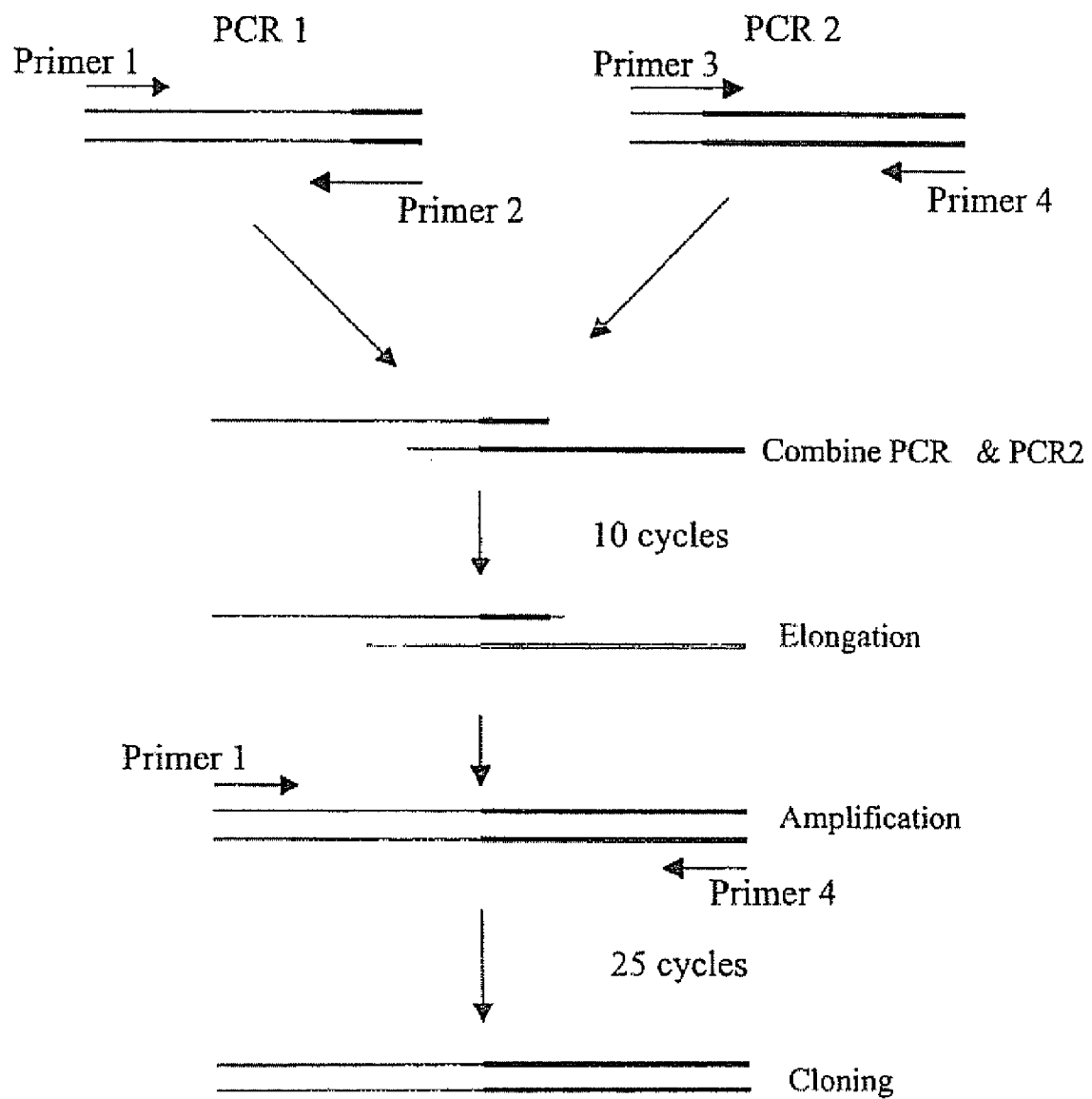
FIG. 1 is a diagrammatic representation of the three steps PCR strategy which can be used to construct a chimeric Dengue 3 virus containing the Yellow Fever NS5 sequence.
Figure 2:
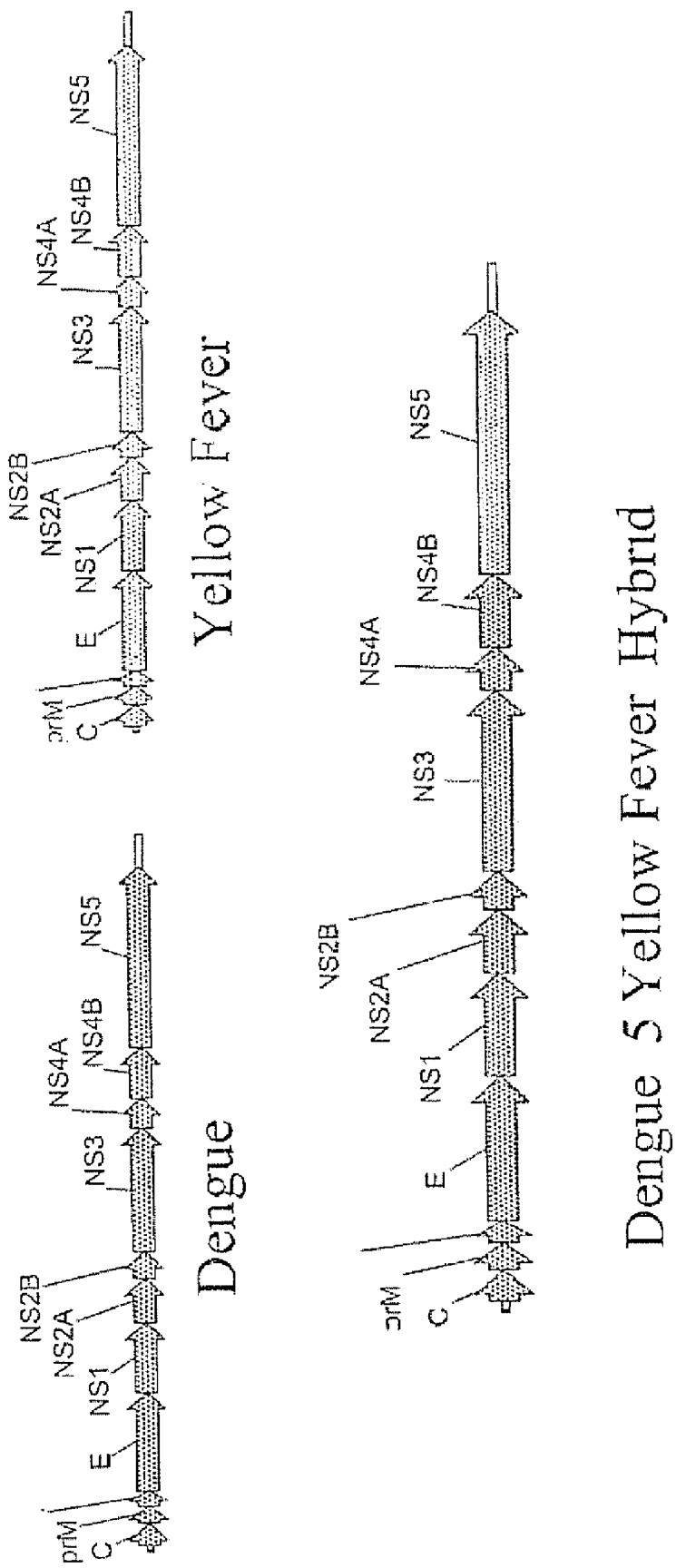
FIG. 2 is a diagrammatic representation of the genomic organization of Dengue virus and Yellow Fever virus, and of the chimeric Dengue 3/Yellow Fever virus.

By the expression "Yellow Fever strain", we mean here any Yellow Fever Strain. As a matter of example a YFD17 strain can be used. This strain has been described by Smithburn et al. (1956) and by Freestone (1995). YF17D has also been studied at the genetic level (Rice et al., 1985) and its genomic sequence is shown in SEQ ID No.7 (Genbank accession number NC 002031). Indeed in the context of the present invention, the NS5 sequence to be inserted in the dengue virus can originate from any Yellow Fever Strain. In one embodiment of the invention, the NS5 encoding sequence of a Dengue virus is replaced by the corresponding NS5 encoding sequence of the YFD 17 strain. Advantageously, the 3'NCR sequence of the same Dengue virus is also replaced by the corresponding 3'NCR sequence of the same Yellow Fever strain.

As used herein, a Dengue (DEN) virus denotes a wild-type Dengue virus of serotype 1, 2, 3 or 4, or a live attenuated Dengue viral strain of serotypes 1, 2, 3, or 4. Dengue viruses are RNA viruses presenting the following gene organization: 5'-noncoding region (NCR), structural protein (capsid (C), premembrane/membrane (prM/M), envelope (E)) and non structural protein (NS1-NS2A-NS2B-NS3-NS4A-NS4B-NS5) and 3' NCR. The RNA genome is associated with the C proteins to form nucleotide (icosadedral symmetry). As with other flaviviruses, the DEN viral genome encodes an uninterrupted open reading frame (ORF) which is translated to a single polyprotein.

In particular, a Dengue serotype 1 (DEN-1) virus may be the wild-type strain 16007. A Dengue serotype 2 (DEN-2) virus may be the wild-type strain 16681. A Dengue serotype 3 (DEN-3) virus may be the wild-type strain 16562 or the newly reintroduced Dengue virus type 3 in Martinique (Peyrefitte et al., 2003; SEQ ID No.8). A dengue serotype 4 (DEN-4) may be the wild type strain 1036.

By "live attenuated" virus or strain, we mean here strain or virus that cause mild (i.e. acceptable in terms of regulatory purposes as presenting a positive benefit/risk ratio) to low or no secondary effects (i.e. systemic events and/or biological abnormalities and/or local reactions) in the majority of the tested humans but still infect and induce an immune response. These live attenuated strains may initially derived from Dengue wild-type strains.

By "immune response", we mean here a response comprising a specific humoral immune response including neutralizing antibodies in primate especially in humans. The induction of a specific humoral immune response can be easily determined by an ELISA assay. The presence of neutralizing antibody in the serum of a vaccine is evaluated by the plaque reduction neutralization test as described in Huang et al (2000). A serum is considered to be positive for the presence of neutralizing antibodies when the neutralizing antibody titer thus determined is at least superior or equal to 1:10.

Dengue strains which can be used as a starting product for the construction of the chimeric dengue virus of the invention are e.g.:

the "LAV1" strain, which is the attenuated strain established after 13 passages of Dengue serotype 1 (DEN-1) strain 16007 in Primary Dog Kidney (PDK). LAV1 sequence is shown in SEQ ID No.9. As compared with DEN-1 16007, LAV1 bears 14 nucleotide substitutions: 1323 T>C, 1541 G>A, 1543 A>G, 1545 G>A, 1567 A>G, 1608 C>T, 2363 A>G, 2695 T>C, 2782 C>T, 5063 G>A, 6048 A>T, 6806 A>G, 7330 A>G, and 9445 C>T. The above-mentioned LAV 1 strain has been described in EP 1159968 in the name of the Mahidol University and was deposited before the Collection Nationale de Culture de Microorganismes (CNCM) on May 25, 2000, under number I-2480.

the "LAV2" strain, which is the attenuated strain established after 53 passages of Dengue serotype 2 (DEN-2) strain 16681 in PDK cells. LAV2 nucleotide sequence is shown in SEQ ID No.10. As compared with the genome sequence of strain 16681, LAV2 bears 9 nucleotide substitutions: 57 C>T, 524 A>T, 2055 C>T, 2579 G>A, 4018 C>T, 5270 A>(A/T), 5547 T>C, 6599 G>C, and 8571 C>T. The above-mentioned LAV2 strain has been described in EP 1159968 in the name of the Mahidol University and was deposited before the CNCM on May 25, 2000, under number I-2481.

the "LAV3" strain, which corresponds to a strain which has been established after 30 passages of Dengue serotype 3 (DEN-3) strain 16562 in Primary Green Monkey Kidney (PGMK) cells and 3 passages in Fetal Rhesus Lung (FRhL) cells. LAV3 nucleotide sequence is shown in SEQ ID No.11. The above-mentioned LAV3 strain has been described in EP 1159968 in the name of the Mahidol University and was deposited before the CNCM on May 25, 2000, under number I-2482.

the "LAV4" strain, which corresponds to a strain which has been established after 18 passages of Dengue serotype 4 (DEN-4) strain 1036 in Primary Dog Kidney (PDK) cells. LAV4 nucleotide sequence is shown in SEQ ID No.12 The above-mentioned LAV4 strain has been described in EP 1159968 in the name of the Mahidol University and was deposited before the CNCM on May 25, 2000, under number I-2483.

Live attenuated Vero-Derived serotype 1 and 2 viruses (VDV1 and VDV2) can also advantageously be used as the starting Dengue strain to construct the chimeric dengue viruses of the invention. VDV1 and VDV2 have been developed by the Applicant through a complex isolation and transfection process comprising various steps including in particular transfecting Vero cells with the purified genomic RNA of respectively LAV1 and LAV2 and plaque purifications. As compared with the genome sequence of strain LAV1, VDV1 (SEQ ID No.13) bears three nucleotide substitutions: 5962 C>A, and 7947 A>G, and optionally 2719 G>A. As compared with the genome sequence of strain LAV2, VDV2 (SEQ ID No.14) bears the following nucleotide substitutions: 736 G>C, 1619 G>A, 4723 T>A, 5062 G>C, 9191 G>A, 10063 T>A, and 10507 A>G, and optionally 1638 A>G, 2520 G>A, and 9222 A>G.

Substitutions identified in Dengue virus genomic sequences or polyproteins are designated pursuant to the nomenclature of Dunnen and Antonarakis (2000). As defined by Dunnen and Antonarakis at the nucleic acid level, substitutions are designated by ">", e.g. "31A>G" denotes that, at nucleotide 31 of the reference sequence, a A is changed to a G.

Chimeric Dengue/Yellow Fever Viruses

The invention thus provides an isolated live chimeric Dengue virus, advantageously an isolated live attenuated chimeric dengue virus, in which the non structural sequence NS5 of the Dengue virus is replaced by the corresponding NS5 sequence of a Yellow Fever virus. Advantageously, the 3'NCR sequence of the Dengue virus is also replaced by the corresponding 3'NCR sequence of the same Yellow Fever virus.

This chimeric Dengue strain can be constructed and isolated using, for example, the protocol described in the attached examples.

These live chimeric dengue strains can be constructed starting from an attenuated dengue strain or from wild type dengue strain. In this latter case, the chimeric virus can then be attenuated, e.g. by serial passage on cell culture such as VERO cells.

Accordingly, in one embodiment, the chimeric dengue virus of the invention is constructed starting from a live attenuated Dengue strain. In a specific embodiment, said one Dengue strain is selected from the group consisting of LAV1 (SEQ ID No.9), LAV2 (SEQ ID No.10), LAV3 (SEQ ID No.11), LAV4 (SEQ ID No.12), Vero-Derived serotype 1 (SEQ ID No.13), and Vero-Derived serotype 2 (SEQ ID No.14).

In a particular embodiment, the NS5 sequence and optionally 3'-NCR sequence incorporated in these above listed attenuated strains are from the Yellow Fever vaccinal strain YF17D (SEQ ID No.7)

The thus produced chimeric dengue viruses can be stored either in the form of a freezed composition or in the form of a lyophilized product. For that purpose, the chimeric dengue virus is mixed with a diluent such as a buffered aqueous solution comprising cryoprotective compounds such sugar alcohol and stabilizer. The pH before freezing or lyophilisation is advantageously settled in the range of 6 to 9, e.g. 7, as determined by a pH meter at room temperature. Before use, the lyophilized product is mixed with a pharmaceutically acceptable diluent or excipient such as a sterile NaCl 4% solution to reconstitute a liquid immunogenic composition or vaccine.

Sequencing at the attenuation-specific loci of the virus recovered after transfection or after serial passages (e.g. 10 passages) on cell cultures allow to confirm the high genetic stability of the chimeric constructs.

Nucleic Acid

The invention also relates to an isolated nucleic acid encoding a chimeric Dengue virus of the invention as defined above. The said nucleic acid thus comprises, or consists of, the 5'-noncoding region (NCR), structural sequences (capsid (C), premembrane/membrane (prM/M), and envelope (E)) and non structural sequences NS1, NS2A, NS2B, NS3, NS4A, and NS4B of one Dengue strain, and the non structural sequence NS5 of a Yellow fever virus and either the 3'-NCR sequence of said Dengue strain or advantageously the 3'-NCR sequence of said Yellow Fever virus.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

The present invention thus provides a cDNA sequence encoding a chimeric Dengue virus of the invention, as well as its equivalent RNA sequence.

By "equivalent RNA sequence" is meant the said DNA sequence wherein deoxythymidines have been replaced by uridines.

The present invention thus also provides the positive strand RNA of the chimeric dengue viruses of the invention.

The invention further relates to the polyprotein encoded by the nucleic acid of the invention.

Immunogenic and Vaccine Compositions

The invention also relates to an immunogenic composition, suitable to be used as a vaccine, which comprises at least one chimeric Dengue virus according to the invention in a pharmaceutically acceptable carrier.

The immunogenic compositions according to the invention elicit a specific humoral immune response toward the dengue virus, including neutralizing antibodies.

According to one embodiment, the immunogenic composition is a vaccine.

According to an embodiment, the immunogenic is a monovalent composition, i.e. a composition which elicits a specific immune response and/or confers protection against the serotype of one Dengue serotype only.

According to another embodiment, the invention relates to a multivalent dengue immunogenic composition, i.e. a composition which elicits a specific immune response against at least 2, such as 3 or 4 dengue serotypes. Such a multivalent immunogenic composition or vaccine may be obtained by combining individual monovalent dengue vaccines. The active component of a multivalent composition of the invention which induces a specific immune response against a second serotype may be a second chimeric Dengue virus of another serotype or a live attenuated Dengue virus of another serotype. For instance, the immunogenic or vaccine multivalent composition of the invention may comprise a chimeric Dengue serotype 1 virus of the invention in combination with at least a chimeric Dengue virus or a live attenuated Dengue virus selected from the group consisting of serotype 2, serotype 3, and serotype 4.

Advantageously, the immunogenic or vaccine composition may be a tetravalent Dengue vaccine composition.

The immunogenic compositions or vaccines according to the present invention may be prepared using any conventional method known to those skilled in the art. Conventionally the antigens according to the invention are mixed with a pharmaceutically acceptable diluent or excipient, such as water or phosphate buffered saline solution, wetting agents, fillers, emulsifier and stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Advantageously, the immunogenic composition or vaccine corresponds to an injectable composition comprising an aqueous buffered solution to maintain e.g. a pH (as determined at RT with a pH meter) in the range of 6 to 9.

The composition according to the invention may further comprise an adjuvant, i.e. a substance which improves, or enhances, the immune response elicited by the chimeric dengue virus(es). Any pharmaceutically acceptable adjuvant or mixture of adjuvants conventionally used in the field of human vaccines may be used for this purpose.

The immunogenic compositions or vaccines according to the invention may be administered by any conventional route usually used in the field of human vaccines, such as the parenteral (e.g. intradermal, subcutaneous, intramuscular) route In the context of the present invention immunogenic compositions or vaccines are preferably injectable compositions administered subcutaneously in the deltoid region.

Method for Immunizing

The invention further provides for a method of immunizing a host in need thereof against a Dengue infection which comprises administering the host with an immunoeffective amount of an immunogenic composition or a vaccine according to the invention.

A "host in need thereof" denotes a person at risk for Dengue infection, i.e. individuals travelling to regions where Dengue virus infection is present, and also inhabitants of those regions.

The route of administration is any conventional route used in the vaccine field. The choice of administration route depends on the formulation that is selected. Preferably, the immunogenic composition or vaccine corresponds to an injectable composition administered via subcutaneous route, advantageously in the deltoid region.

The amount of live attenuated chimeric Dengue virus in the immunogenic compositions or vaccines may be conveniently expressed in viral plaque forming unit (PFU) unit or Cell Culture Infectious Dose 50% ($CCID_{50}$) dosage form and prepared by using conventional pharmaceutical techniques. For instance, the composition according to the invention may be prepared in dosage form containing 10 to $10^6$ $CCID_{50}$, or from $10^3$ to $10^5$ $CCID_{50}$ of virus, for instance $4\pm0.5$ $\log_{10}$ $CCID_{50}$ of live attenuated chimeric Dengue virus for a monovalent composition. Where the composition is multivalent, to reduce the possibility of viral interference and thus to achieve a balanced immune response (i.e. an immune response against all the serotype contained in the composition), the amounts of each of the different dengue serotypes present in the administered vaccines may not be equal.

An "immunoeffective amount" is an amount which is capable of inducing a specific humoral immune response comprising neutralising antibodies in the serum of a vaccinee. Methods for evaluating the presence of neutralizing antibodies are well known by the one skilled in the art.

The volume of administration may vary depending on the route of administration. Subcutaneous injections may range in volume from about 0.1 ml to 1.0 ml, preferably 0.5 ml.

The optimal time for administration of the composition is about one to three months before the initial exposure to the dengue virus. The vaccines of the invention can be administered as prophylactic agents in adults or children at risk of Dengue infection. The targeted population thus encompasses persons which are naïve as well as well as non-naïve with regards to dengue virus. The vaccines of the invention can be administered in a single dose or, optionally, administration can involve the use of a priming dose followed by a booster dose that is administered, e.g. 2-6 months later, as determined to be appropriate by those of skill in the art.

The invention will be further described in view of the following figures and examples. For sake of clarity the following description details only the construction of a chimeric dengue virus of the invention from a LAV3 backbone.

EXAMPLES

Example 1

Construction of a Chimeric Dengue 3 Virus Containing the Yellow Fever NS5 Sequence To construct a chimeric dengue 3 virus of the invention, The complete Dengue 3 genomic cDNA (SEQ ID No.11) can be cloned into a vector pVAX (Invitrogen) containing the T7 RNA polymerase promoter and engineered such that the unique NotI restriction site is flanking the 3' end of the viral sequence.

To link Dengue 3 NS4b and Yellow Fever NS5 one can use the following strategy based on the technique of overlap extension. This technique is advantageously selected for it's capacity to perfectly fuse two genetic sequence avoiding the need to create new restriction sites at the point of junction.

The Dengue-Yellow Fever chimeric construct can be generated using three consecutive PCR steps, as shown on the diagrammatic representation on FIG. 1 and as described below.

Figure 3:
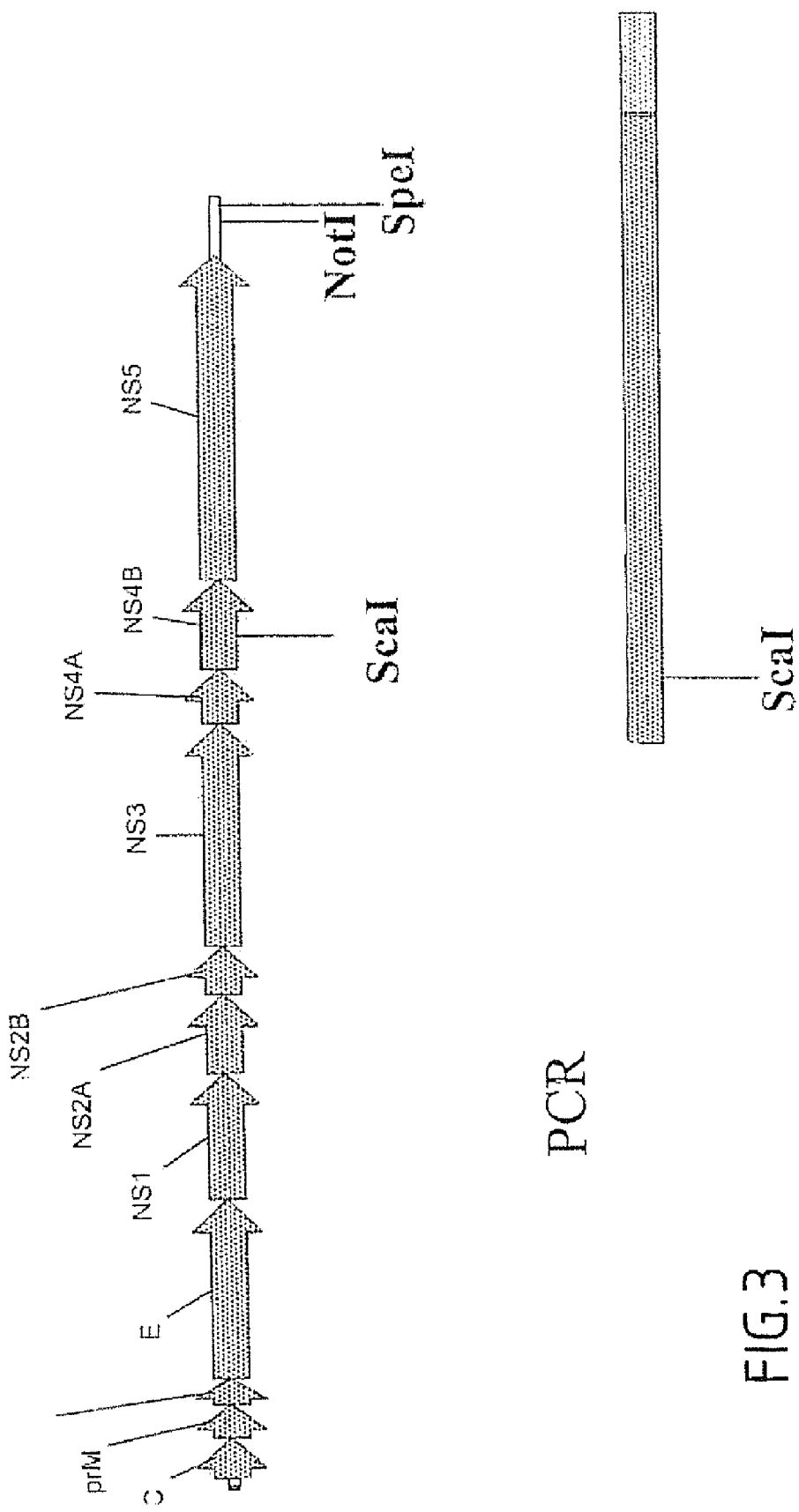
FIG. 3 shows the position of the ScaI restriction sites on Dengue-3 genome and on the amplicon PCR1.

In the first PCR step, two partially overlapping DNA fragments (PCR1 and PCR2) are generated as follows:

The PCR1 fragment is generated according to the strategy displayed on FIG. 3.

PCR 1

| Plasmid DNA (50 ng/µl) | 0.5 µl |
|---|---|
| 10x Buffer | 5 µl |
| Primer 1 (125 ng/µl) | 1 µl |
| Primer 2 (125 ng/µl) | 1 µl |
| dNTP 1.25 mM | 8 µl |
| Nuclease-free water | 34.5 µl |
| Final volume | 50 µl |

+1 µl de Platinum Hi Fi Taq polymerase with

Primer-1:
(SEQ ID No. 1)
CGGCAGTACTTTTGCTAATCACACATTATG

Primer-2:
(SEQ ID No. 2)
TTTTTCCATTCGCGCTCCCTCTTTTTCCTGTTCCAACTG

Primer 1 is located into the NS4b of Dengue 3 (nucleotides 7146 to 7175 of Dengue 3 sequence SEQ ID No.9) and contains the unique ScaI restriction site (underlined). Primer 2 overlaps NS4b Dengue 3 (bold characters) and NS5 Yellow Fever sequences.

Program:

| Initial denaturation | 95° C. | 30 sec | |
|---|---|---|---|
| Denaturation | 95° C. | 30 sec | |
| Hybridization | 57° C. | 1 min | for 30 cycles |
| Elongation | 68° C. | 1 min | |

A 0.45 Kb fragment containing about 430 nucleotides of the Dengue NS4b sequence and a small extension corresponding to the 5' end of the Yellow Fever NS5 sequence can thus be obtained (PCR1, SEQ ID No.3).

Figure 4:
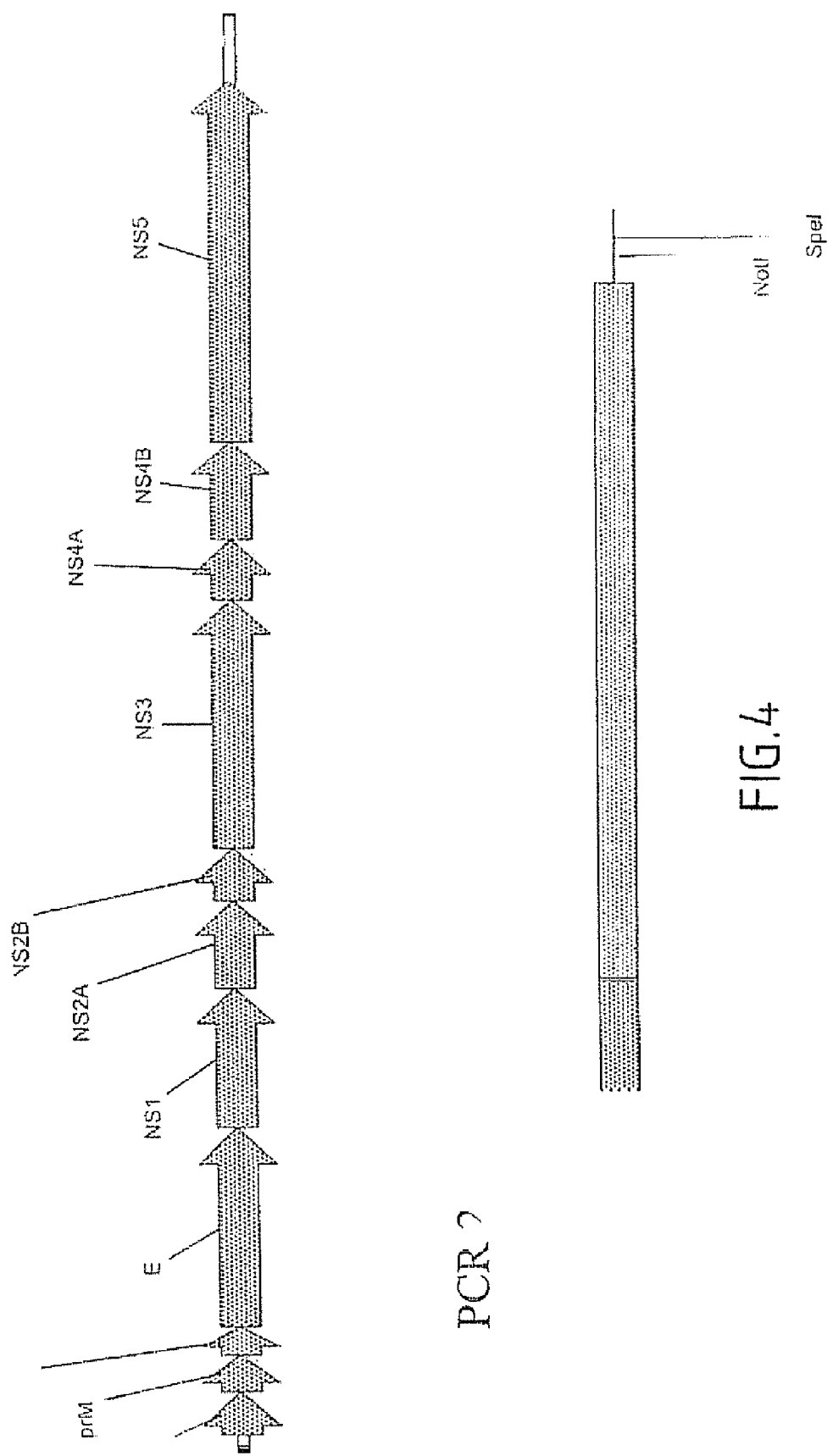
FIG. 4 shows the position of the NotI and SpeI restriction sites on Dengue-3 genome and on the amplicon PCR2.

The PCR2 fragment is generated according to the strategy displayed on FIG. 4.

PCR 2

| cDNA from YF virus (50 ng/µl) | 0.5 µl |
|---|---|
| 10x Buffer | 5 µl |
| Primer 3 (125 ng/µl) | 1 µl |

-continued

| | |
|---|---|
| Primer 4 (125 ng/μl) | 1 μl |
| dNTP 1.25 mM | 8 μl |
| Nuclease-free water | 34.5 μl |
| Final volume | 50 μl |

+1 μl de Platinum Hi Fi Taq polymerase
with

Primer-3
(SEQ ID No. 4)
CAGTTGGAACAGGAAAAAGAGGGAGCGCGAATGGAAAAA

Primer-4
(SEQ ID No. 5)
GGACTAGTAACGCCGGCGAGTGGTTTTGTGTTTGTCATC

Primer 3 overlaps NS4b Dengue 3 and NS5 Yellow Fever (bold characters) and is the reverse complement of primer 2. Primer 4 is located into the 3'UTR of Yellow Fever and contains Not I and Spe I restriction sites (underlined)
Program:

| | | | |
|---|---|---|---|
| Initial denaturation | 95° C. | 30 sec | |
| Denaturation | 95° C. | 30 sec | |
| Hybridization | 57° C. | 1 min | 30 cycles |
| Elongation | 68° C. | 4 min | |

A 3.2 Kb fragment containing 15 Nucleotides of the 5' end of the Dengue NS4b sequence and the complete sequence encoding the Yellow Fever NS5 encoding sequence and the 3' region non coding sequence of the Yellow Fever genome can thus be obtained (PCR2, SEQ ID No.6).

Figure 5:
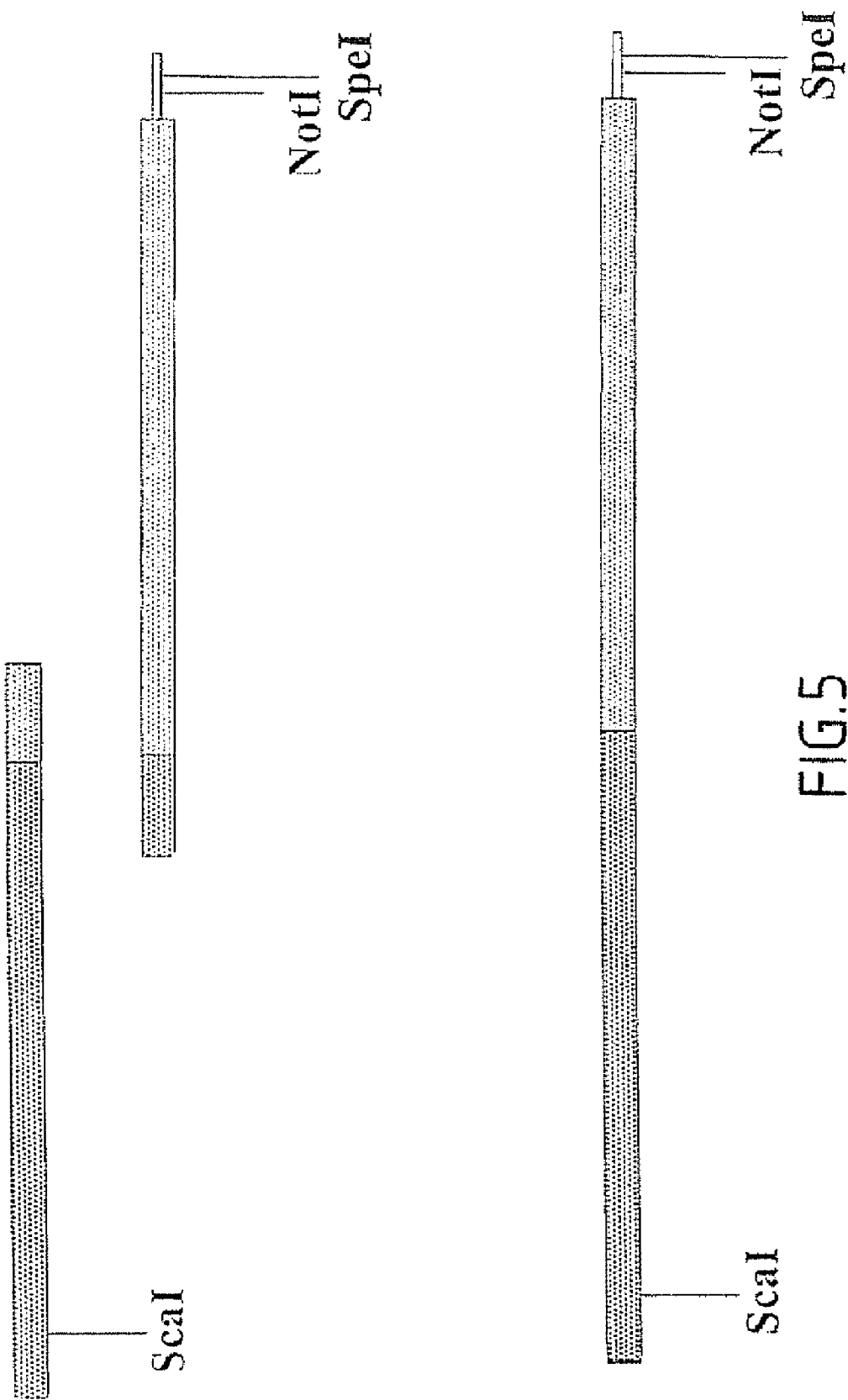
FIG. 5 shows overlapping between amplicons PCR1 and PCR2.

In a second PCR step (reaction PCR3, FIG. 5), a stoechiometric mixture of both partially overlapping fragments PCR1 and PCR2 is submitted to 10 PCR cycles. No primer is added.
PCR 3

| | |
|---|---|
| Product of PCR 1 | 0.5 μl |
| Product of PCR 2 | 0.5 μl |
| 10x Buffer | 5 μl |
| dNTP 1.25 mM | 8 μl |
| Nuclease-free water | 36 μl |
| Final volume | 50 μl |

+1 μl de Platinum Hi Fi Taq polymerase

Program:

| | | | |
|---|---|---|---|
| Initial denaturation | 95° C. | 30 sec | |
| Denaturation | 95° C. | 30 sec | |
| Hybridisation | 57° C. | 1 min | 10 cycles |
| Elongation | 68° C. | 4 min | |

The third PCR step (reaction PCR4) is carried out with the product of the second reaction in the presence of primers 1 and 4 containing respectively the ScaI and Not/Spe restriction sites. To that end 1 μl of each of primer 1 and primer 4 (125 ng/μl) is added to the reaction product of PCR3 and the PCR reaction is continued for 25 additional cycles.

The resulting large DNA fragment can be purified on agarose gel, then digested with ScaI and NotI or SpeI restriction endonucleases and ligated to the original vector containing the whole Dengue 3 sequence.

Example 2

Recovery of Chimeric Dengue Viruses

To recover the chimeric dengue viruses, the following strategy can be used.

All recombinant plasmids can be amplified in *Escherichia coli* XL1-Blue cells. 500 ng of plasmid are then linearized by the NotI restriction endonuclease. Viral RNA can be obtained after in vitro transcription using T7 RNA polymerase and capped with the cap analog $m^7$ GpppA. And, then transfected into $3\times10^6$ to $4\times10^6$ LLC-$MK_2$ or BHK-21 cells by electroporation. Transfected cells are transferred to 75-$cm^2$ flasks in DMEM containing 10% FBS. The resulting chimeric virus is then amplified and isolated from the cells.

REFERENCES

Dunnen and Antonarakis (2000) Mutation nomenclature extensions and suggestions to describe complex mutations: a discussion. Hum Mutation. 15 :7-12; Erratum in: Hum Mutat 2002; 20(5):403
Freestone, in Plotkin et al., eds, Vaccines, $2^{nd}$ ed, W.B. Saunders, PA, 1995
Gubler D J. Dengue. (1988) In: Epidemiology of arthropod-borne viral disease.
Monath T P M, editor, Boca Raton (Fla.): CRC Press: 223-60
Gubler D J, Kuno G. Dengue and Dengue Hemorrhagic Fever. CAB International Publishing 1997
Huang et al. (2000), J. Virol. 74; 3020-3028
Kautner I, Robinson M J, Kubnle U. (1997) Dengue Virus infection: Epidemiology, pathogenesis, clinical presentation, diagnosis, and prevention. J of Pediatrics; 131:516-524
Peyrefitte, C. N., Couissinier-Paris, P., Mercier-Perennec, V., Bessaud, M., Martial, J., Kenane, N., Durand, J. P. and Tolou, H. J. (2003) Genetic Characterization of Newly Reintroduced Dengue Virus Type 3 in Martinique (French West Indies). J. Clin. Microbiol. 41 (11), 5195-5198
Pugachev K V et al., (2004) High Fidelity of Yellow Fever Virus RNA Polymerase. Journal of Virology, 78, p. 1032-1038
Rice, C. M., Lenches, E. M., Eddy, S. R., Shin, S. J., Sheets, R. L. and Strauss, J. H. (1985) Nucleotide sequence of yellow fever virus: implications for flavivirus gene expression and evolution. Science; 229, 726-733
Rigau-Pérez J G, Clark G G, Gubler D J, Reiter P, Sanders E J, Vorndam A V. (1998) Dengue and dengue haemorrhagic fever. Lancet; 352: 971-977.
Rothman A L, Ennis F A. (1999) Immunopathogenesis of dengue haemorrhagic fever. Virology; 257: 1-6
Sabin A B. (1952) Research on dengue during World War II. Am J Trop Med Hyg; 1: 30-50
Smithburn et al., (1956) Yellow Fever Vaccination, World Health Org. p. 238
Vaughn D W, Green S, Kalayanarooj S, Innis B L, Nimmannitya S, Suntayakorn S, Rothman A L, Ennis F A, Nisalak A. (1997) Dengue in the early febrile phase: viremia and antibody response. J Infect Dis; 176: 322-30
Vaughn D W, Green S, Kalayanarooj S, Innis B L, Nimmannitya S, Suntayakorn S, Endy T P, Raengsakulrach B, Rothman A L, Ennis F A, Nisalak A. (2000) Dengue viremia titer, antibody response pattern, and virus serotype correlate with disease severity. J Inf Dis; 181: 2-9
WHO Technical Guide, (1986) Dengue haemorrhagic fever: diagnosis, treatment and control, p 1-2. World Health Organization, Geneva, Switzerland
Wu S, Grouard-Vogel G, Sun W, Mascola J, Brachtel E, Putvatana R. (2000) Human skin Langerhans cells are targets of dengue virus infection. Nature Med; 7:816-820

The invention claimed is:

1. An isolated, attenuated chimeric Dengue virus comprising the 5'-noncoding region (NCR), structural sequences capsid (C), premembrane/membrane (prM/M), and envelope (E), and non structural sequences NS1, NS2A, NS2B, NS3, NS4A, and NS4B of one Dengue strain; the non structural sequence NS5 of a Yellow fever virus; and either the 3'-NCR sequence of said Dengue strain or the 3'-NCR sequence of said Yellow Fever virus.

2. The isolated chimeric Dengue virus of claim 1, wherein the 3' NCR sequence of the Dengue virus has been replaced by the 3'NCR sequence of the same Yellow Fever virus.

3. The isolated chimeric Dengue virus according to claim 1, wherein said Dengue virus is selected from the group consisting of Dengue serotype 1, Dengue serotype 2, Dengue serotype 3, and Dengue serotype 4 viruses.

4. The isolated chimeric Dengue virus according to claim 1, wherein said Dengue virus is a live attenuated Dengue virus.

5. The isolated chimeric Dengue virus according to claim 1, wherein said one Dengue strain is LAV1 (SEQ ID No.9).

6. The isolated chimeric Dengue virus according to claim 1, wherein said Yellow Fever virus is the vaccinal strain YF17D (SEQ ID No.7).

7. An immunogenic composition comprising a chimeric Dengue virus according to claim 1 or 2 in a pharmaceutically acceptable carrier.

8. The immunogenic composition according to claim 7, which is a monovalent composition.

9. The immunogenic composition according to claim 7, which is a multivalent composition.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Artificial
<220> FEATURE:
<223> OTHER INFORMATION: Synthetic, PCR primer for NS4b of Dengue 3

<400> SEQUENCE: 1
cggcagtact tttgctaatc acacattatg                                      30

<210> SEQ ID NO 2
<211> LENGTH: 39
<212> TYPE: DNA
<213> ORGANISM: Artificial
<220> FEATURE:
<223> OTHER INFORMATION: Synthetic, PCR primer for NS4b of Dengue 3 and
      NS5 of Yellow Fever Virus

<400> SEQUENCE: 2
tttttccatt cgcgctccct cttttttcctg ttccaactg                            39

<210> SEQ ID NO 3
<211> LENGTH: 438
<212> TYPE: DNA
<213> ORGANISM: Artificial
<220> FEATURE:
<223> OTHER INFORMATION: Synthetic, product of PCR reaction

<400> SEQUENCE: 3
cggcagtact cttgctgatc acacattatg ctattatagg tccaggattg caggcaaaag      60
ccactcgtga agctcagaaa aggacagctg ctggaataat gaagaatcca acggtggatg     120
ggataatgac aatagaccta gatcctgtaa tatatgattc aaaatttgaa agcaactgg      180 gacaggttat gctcctggtt tgtgtgcag ttcaacttttt gttaatgaga acatcatggg    240
ccttgtgtga agctttaact ctagctacag gaccaataac aacactctgg gaaggatcac     300
ctgggaagtt ttggaacacc acgatagctg tttccatggc gaacatttttt agagggagct     360 atttagcagg agctgggctt gctttttcta ttatgaaatc agttggaaca ggaaaaagag     420
ggagcgcgaa tggaaaaa                                                  438

<210> SEQ ID NO 4
<211> LENGTH: 39
<212> TYPE: DNA
<213> ORGANISM: Artificial
<220> FEATURE:
<223> OTHER INFORMATION: Synthetic, PCR primer for NS4b Dengue 3 and NS5
      Yellow Fever

<400> SEQUENCE: 4
cagttggaac aggaaaaaga gggagcgcga atggaaaaa                            39

<210> SEQ ID NO 5
<211> LENGTH: 39
<212> TYPE: DNA
<213> ORGANISM: Artificial
<220> FEATURE:
<223> OTHER INFORMATION: Synthetic, PCR primer for 3' UTR of Yellow
      Fever virus

<400> SEQUENCE: 5
ggactagtaa cgccggcgag tggttttgtg tttgtcatc                            39

<210> SEQ ID NO 6
<211> LENGTH: 3246
<212> TYPE: DNA
<213> ORGANISM: Artificial
<220> FEATURE:
<223> OTHER INFORMATION: Synthetic, product of PCR reaction

<400> SEQUENCE: 6

| | | | | | |
|---|---|---|---|---|---|
| cagttggaac | aggaaaaaga | gggagcgcga | atggaaaaac | tttgggtgaa | gtctggaaga | 60 |
| gggaactgaa | tctgttggac | aagcgacagt | ttgagttgta | taaaaggacc | gacattgtgg | 120 |
| aggtggatcg | tgatacggca | cgcaggcatt | tggccgaagg | gaaggtggac | accggggtgg | 180 |
| cggtctccag | ggggaccgca | aagttaaggt | ggttccatga | gcgtggctat | gtcaagctgg | 240 |
| aaggtagggt | gattgacctg | gggtgtggcc | gcggaggctg | tgttactac | gctgctgcgc | 300 |
| aaaaggaagt | gagtggggtc | aaaggattta | ctcttggaag | agacggccat | gagaaaccca | 360 |
| tgaatgtgca | aagtctggga | tggaacatca | tcaccttcaa | ggacaaaact | gatatccacc | 420 |
| gcctagaacc | agtgaaatgt | gacacccttt | tgtgtgacat | tggagagtca | tcatcgtcat | 480 |
| cggtcacaga | gggggaaagg | accgtgagag | ttcttgatac | tgtagaaaaa | tggctggctt | 540 |
| gtggggttga | caacttctgt | gtgaaggtgt | tagctccata | catgccagat | gttctcgaga | 600 |
| aactggaatt | gctccaaagg | aggtttggcg | aacagtgat | caggaaccct | ctctccagga | 660 |
| attccactca | tgaaatgtac | tacgtgtctg | agcccgcag | caatgtcaca | tttactgtga | 720 |
| accaaacatc | ccgcctcctg | atgaggagaa | tgaggcgtcc | aactggaaaa | gtgaccctgg | 780 |
| aggctgacgt | catcctccca | attgggacac | gcagtgttga | gacagacaag | gacccctgg | 840 |
| acaaagaggc | catagaagaa | agggttgaga | ggataaaatc | tgagtacatg | acctcttggt | 900 |
| tttatgacaa | tgacaacccc | tacaggacct | ggcactactg | tggctcctat | gtcacaaaaa | 960 |
| cctcaggaag | tgcggcgagc | atggtaaatg | gtgttattaa | aattctgaca | tatccatggg | 1020 |
| acaggataga | ggaggtcaca | agaatggcaa | tgactgacac | aaccccttt | ggacagcaaa | 1080 |
| gagtgtttaa | agaaaaagtt | gacaccagag | caaaggatcc | accagcggga | actaggaaga | 1140 |
| tcatgaaagt | tgtcaacagg | tggctgttcc | gccacctggc | cagagaaaag | aaccccagac | 1200 |
| tgtgcacaaa | ggaagaattt | attgcaaaag | tccgaagtca | tgcagccatt | ggagcttacc | 1260 |
| tggaagaaca | agaacagtgg | aagactgcca | atgaggctgt | ccaagaccca | agttctgggg | 1320 |
| aactggtgga | tgaagaaagg | aagctgcacc | aacaaggcag | gtgtcggact | tgtgtgtaca | 1380 |
| acatgatggg | gaaaagagag | aagaagctgt | cagagtttgg | gaaagcaaag | ggaagccgtg | 1440 |
| ccatatggta | tatgtggctg | ggagcgcggt | atcttgagtt | tgaggccctg | ggattcctga | 1500 |
| atgaggacca | ttgggcttcc | agggaaaact | caggaggagg | agtggaaggc | attggcttac | 1560 |
| aataccatgg | atatgtgatc | agagacctgg | ctgcaatgga | tggtggtgga | ttctacgcgg | 1620 |
| atgacaccgc | tggatgggac | acgcgcatca | cagaggcaga | ccttgatgat | gaacaggaga | 1680 |
| tcttgaacta | catgagccca | catcacaaaa | aactggcaca | agcagtgatg | gaaatgacat | 1740 |
| acaagaacaa | agtggtgaaa | gtgttgagac | cagcccagg | agggaaagcc | tacatggatg | 1800 |
| tcataagtcg | acgagaccag | agaggatccg | ggcaggtagt | gacttatgct | ctgaacacca | 1860 |
| tcaccaactt | gaaagtccaa | ttgatcagaa | tggcagaagc | agagatggtg | atacatcacc | 1920 |
| aacatgttca | agattgtgat | gaatcagttc | tgaccaggct | ggaggcatgg | ctcactgagc | 1980 |
| acggatgtga | cagactgaag | aggatggcgg | tgagtggaga | cgactgtgtg | gtccggccca | 2040 |
| tcgatgacag | gttcggcctg | gccctgtccc | atctcaacgc | catgtccaag | gttagaaagg | 2100 |

```
acatatctga atggcagcca tcaaaagggt ggaatgattg ggagaatgtg cccttctgtt    2160
cccaccactt ccatgaacta cagctgaagg atggcaggag gattgtggtg ccttgccgag    2220
aacaggacga gctcattggg agaggaaggg tgtctccagg aaacggctgg atgatcaagg    2280
aaacagcttg cctcagcaaa gcctatgcca acatgtggtc actgatgtat tttcacaaaa    2340
gggacatgag gctactgtca ttggctgttt cctcagctgt tcccacctca tgggttccac    2400
aaggacgcac aacatggtcg attcatggga aaggggagtg gatgaccacg aagacatgc     2460 ttgaggtgtg aacagagta tggataacca acaacccaca catgcaggac aagacaatgg     2520
tgaaaaaatg gagagatgtc ccttatctaa ccaagagaca agacaagctg tgcggatcac    2580
tgattggaat gaccaatagg gccacctggg cctcccacat ccatttagtc atccatcgta    2640
tccgaacgct gattggacag gagaaataca ctgactacct aacagtcatg gacaggtatt    2700
ctgtggatgc tgacctgcaa ctgggtgagc ttatctgaaa caccatctaa caggaataac    2760
cgggatacaa accacgggtg gagaaccgga ctccccacaa cctgaaaccg gatataaac    2820 cacggctgga gaaccgggct ccgcacttaa aatgaaacag aaaccgggat aaaaactacg    2880
gatggagaac cggactccac acattgagac agaagaagtt gtcagcccag aaccccacac    2940
gagttttgcc actgctaagc tgtgaggcag tgcaggctgg gacagccgac ctccaggttg    3000
cgaaaaacct ggtttctggg acctcccacc ccagagtaaa aagaacggag cctccgctac    3060
caccctccca cgtggtggta aaagacgggg gtctagaggt tagaggagac cctccaggga    3120
acaaatagtg ggaccatatt gacgccaggg aagaccgga gtggttctct gcttttcctc     3180
cagaggtctg tgagcacagt ttgctcaaga ataagcagac ctttggatga caaacacaaa    3240
accact                                                              3246

<210> SEQ ID NO 7
<211> LENGTH: 10862
<212> TYPE: DNA
<213> ORGANISM: Yellow fever virus

<400> SEQUENCE: 7
agtaaatcct gtgtgctaat tgaggtgcat tggtctgcaa atcgagttgc taggcaataa      60
acacatttgg attaatttta atcgttcgtt gagcgattag cagagaactg accagaacat     120
gtctggtcgt aaagctcagg gaaaaaccct gggcgtcaat atggtacgac gaggagttcg     180
ctccttgtca aacaaaataa acaaaaaac aaaacaaatt ggaaacagac ctggaccttc      240
aagaggtgtt caaggattta tcttttcttt tttgttcaac attttgactg gaaaaaagat     300
cacagcccac ctaaagaggt tgtggaaaat gctggaccca agacaaggct tggctgttct    360
aaggaaagtc aagagagtgg tggccagttt gatgagagga ttgtcctcaa ggaaacgccg     420
ttcccatgat gttctgactg tgcaattcct aattttggga atgctgttga tgacgggtgg    480
agtgaccttg gtgcggaaaa acagatggtt gctcctaaat gtgacatctg aggacctcgg    540
gaaaacattc tctgtgggca caggcaactg cacaacaaac attttggaag ccaagtactg    600
gtgcccagac tcaatggaat acaactgtcc caatctcagt ccaagagagg agccagatga    660
cattgattgc tggtgctatg gggtggaaaa cgttagagtc gcatatggta agtgtgactc    720
agcaggcagg tctaggaggt caagaagggc cattgacttg cctacgcatg aaaaccatgg    780
tttgaagacc cggcaagaaa aatggatgac tggaagaatg ggtgaaaggc aactccaaaa    840
gattgagaga tggttcgtga ggaaccccct ttttgcagtg acggctctga ccattgcctca   900 ccttgtggga agcaacatga cgcaacgagt cgtgattgcc ctactggtct tggctgttgg    960
```

```
tccggcctac tcagctcact gcattggaat tactgacagg gatttcattg aggggggtgca    1020
tggaggaact tgggtttcag ctaccctgga gcaagacaag tgtgtcactg ttatggcccc    1080
tgacaagcct tcattggaca tctcactaga gacagtagcc attgatagac ctgctgaggt    1140
gaggaaagtg tgttacaatg cagttctcac tcatgtgaag attaatgaca agtgccccag    1200
cactggagag gcccacctag ctgaagagaa cgaaggggac aatgcgtgca agcgcactta    1260
ttctgataga ggctggggca atggctgtgg cctatttggg aaagggagca ttgtggcatg    1320
cgccaaattc acttgtgcca aatccatgag tttgtttgag gttgatcaga ccaaaattca    1380
gtatgtcatc agagcacaat tgcatgtagg ggccaagcag gaaaattgga ataccgacat    1440
taagactctc aagtttgatg ccctgtcagg ctcccaggaa gtcgagttca ttgggtatgg    1500
aaaagctaca ctggaatgcc aggtgcaaac tgcggtggac tttggtaaca gttacatcgc    1560
tgagatggaa acagagagct ggatagtgga cagacagtgg gcccaggact tgaccctgcc    1620
atggcagagt ggaagtggcg gggtgtggag agagatgcat catcttgtcg aatttgaacc    1680
tccgcatgcc gccactatca gagtactggc cctgggaaac caggaaggct ccttgaaaac    1740
agctcttact ggcgcaatga gggttacaaa ggacacaaat gacaacaacc tttacaaact    1800
acatggtgga catgtttctt gcagagtgaa attgtcagct ttgacactca aggggacatc    1860
ctacaaaata tgcactgaca aaatgttttt tgtcaagaac ccaactgaca ctggccatgg    1920
cactgttgtg atgcaggtga aagtgtcaaa aggagccccc tgcaggattc cagtgatagt    1980
agctgatgat cttacagcgg caatcaataa aggcattttg gttacagtta accccatcgc    2040
ctcaaccaat gatgatgaag tgctgattga ggtgaaccca ccttttggag acagctacat    2100
tatcgttggg agaggagatt cacgtctcac ttaccagtgg cacaaagagg gaagctcaat    2160
aggaaagttg ttcactcaga ccatgaaagg cgtggaacgc ctggccgtca tgggagacac    2220
cgcctgggat ttcagctccg ctggagggtt cttcacttcg gttgggaaag gaattcatac    2280
ggtgtttggc tctgcctttc aggggctatt tggcggcttg aactggataa caaaggtcat    2340
catgggggcg gtacttatat gggttggcat caacacaaga aacatgacaa tgtccatgag    2400
catgatcttg gtaggagtga tcatgatgtt tttgtctcta ggagttgggg cggatcaagg    2460
atgcgccatc aactttggca agagagagct caagtgcgga gatggtatct tcatatttag    2520
agactctgat gactggctga caagtactc atactatcca gaagatcctg tgaagcttgc    2580
atcaatagtg aaagcctctt ttgaagaagg gaagtgtggc ctaaattcag ttgactccct    2640
tgagcatgag atgtggagaa gcagggcaga tgagatcaat gccattttg aggaaaacga    2700
ggtggacatt tctgttgtcg tgcaggatcc aaagaatgtt taccagagag gaactcatcc    2760
atttttccaga attcgggatg gtctgcagta tggttggaag acttggggta agaaccttgt    2820
gttctcccca gggaggaaga atggaagctt catcatagat ggaaagtcca ggaaagaatg    2880
cccgttttca aaccgggtct ggaattcttt ccagatagag gagtttggga cgggagtgtt    2940
caccacacgc gtgtacatgg acgcagtctt tgaatacacc atagactgcg atggatctat    3000
cttgggtgca gcggtgaacg gaaaaaagag tgcccatggc tctccaacat ttgatgggg    3060
aagtcatgaa gtaaatggga catggatgat ccacacctttg gaggcattag attacaagga    3120
gtgtgagtgg ccactgacac atacgattgg aacatcagtt gaagagagtg aaatgttcat    3180
gccgagatca atcggaggcc cagttagctc tcacaatcat atccctggat acaaggttca    3240
gacgaacgga ccttgatgc aggtaccact agaagtgaag agagaagctt gcccaggggac    3300
tagcgtgatc attgatggca actgtgatgg acggggaaaa tcaaccagat ccaccacgga    3360
```

```
tagcgggaaa gttattcctg aatggtgttg ccgctcctgc acaatgccgc ctgtgagctt    3420
ccatggtagt gatgggtgtt ggtatcccat ggaaattagg ccaaggaaaa cgcatgaaag    3480
ccatctggtg cgctcctggg ttacagctgg agaaatacat gctgtcccct ttggtttggt    3540
gagcatgatg atagcaatgg aagtggtcct aaggaaaaga cagggaccaa agcaaatgtt    3600
ggttggagga gtagtgctct tgggagcaat gctggtcggg caagtaactc tccttgattt    3660
gctgaaactc acagtggctg tgggattgca tttccatgag atgaacaatg gaggagacgc    3720
catgtatatg gcgttgattg ctgccttttc aatcagacca gggctgctca tcggcttttgg   3780 gctcaggacc ctatggagcc ctcgggaacg ccttgtgctg accctaggag cagccatggt    3840
ggagattgcc ttgggtggcg tgatgggcgg cctgtggaag tatctaaatg cagtttctct    3900
ctgcatcctg acaataaatg ctgttgcttc taggaaagca tcaaatacca tcttgcccct    3960
catggctctg ttgacacctg tcactatggc tgaggtgaga cttgccgcaa tgttcttttg    4020
tgccgtggtt atcatagggg tccttcacca gaatttcaag gacacctcca tgcagaagac    4080
tatacctctg gtggccctca cactcacatc ttacctgggc ttgacacaac cttttttggg    4140
cctgtgtgca tttctggcaa cccgcatatt tgggcgaagg agtatcccag tgaatgaggc    4200
actcgcagca gctggtctag tgggagtgct ggcaggactg gcttttcagg agatggagaa    4260
cttccttggt ccgattgcag ttggaggact cctgatgatg ctggttagcg tggctggagg   4320
ggtggatggg ctagagctca agaagcttgg tgaagtttca tgggaagagg aggcggagat    4380
cagcgggagt tccgcccgct atgatgtggc actcagtgaa caaggggagt tcaagctgct    4440
ttctgaagag aaagtgccat gggaccaggt tgtgatgacc tcgctggcct tggttgggc    4500 tgccctccat ccatttgctc ttctgctggt ccttgctggg tggctgtttc atgtcagggg    4560
agctaggaga agtggggatg tcttgtggga tattcccact cctaagatca tcgaggaatg    4620
tgaacatctg gaggatggga tttatggcat attccagtca accttcttgg gggcctccca    4680
gcgaggagtg ggagtggcac agggaggggt gttccacaca atgtggcatg tcacaagagg    4740 agcttttcctt gtcaggaatg gcaagaagtt gattccatct tgggcttcag taaaggaaga    4800
ccttgtcgcc tatggtggct catggaagtt ggaaggcaga tgggatggag aggaagaggt    4860
ccagttgatc gcggctgttc caggaaagaa cgtggtcaac gtccagacaa aaccgagctt    4920
gttcaaagtg aggaatgggg gagaaatcgg ggctgtcgct cttgactatc cgagtggcac    4980
ttcaggatct cctattgtta acaggaacgg agaggtgatt gggctgtacg gcaatggcat    5040
ccttgtcggt gacaactcct tcgtgtccgc catatcccag actgaggtga aggaagaagg    5100
aaaggaggag ctccaagaga tcccgacaat gctaaagaaa ggaatgacaa ctgtccttga    5160
ttttcatcct ggagctggga gacaagacg tttcctccca cagatcttgg ccgagtgcgc    5220
acggagacgc ttgcgcactc ttgtgttggc ccccaccagg gttgttcttt ctgaaatgaa    5280 ggaggcttttt cacggcctgg acgtgaaatt ccacacacag gcttttttccg ctcacggcag    5340 cgggagagaa gtcattgatg ccatgtgcca tgccacccta acttacagga tgttggaacc    5400
aactagggtt gttaactggg aagtgatcat tatggatgaa gcccatttt tggatccagc    5460 tagcatagcc gctagaggtt gggcagcgca cagagctagg gcaaatgaaa gtgcaacaat    5520
cttgatgaca gccacaccgc ctgggactag tgatgaattt ccacattcaa atggtgaaat    5580
agaagatgtt caaacggaca tacccagtga gccctggaac acagggcatg actggatcct    5640
agctgacaaa aggcccacgg catggttcct tccatccatc agagctgcaa atgtcatggc    5700
tgcctctttg cgtaaggctg gaaagagtgt ggtggtcctg aacagaaaa cctttgagag    5760
```

```
agaatacccc acgataaagc agaagaaacc tgactttata ttggccactg acatagctga    5820
aatgggagcc aacctttgcg tggagcgagt gctggattgc aggacggctt ttaagcctgt    5880
gcttgtggat gaagggagga aggtggcaat aaaagggcca cttcgtatct ccgcatcctc    5940
tgctgctcaa aggaggggc gcattgggag aaatcccaac agagatggag actcatacta    6000
ctattctgag cctacaagtg aaaataatgc ccaccacgtc tgctggttgg aggcctcaat    6060
gctcttggac aacatggagg tgaggggtgg aatggtcgcc ccactctatg gcgttgaagg    6120
aactaaaaca ccagtttccc ctggtgaaat gagactgagg gatgaccaga ggaaagtctt    6180
cagagaacta gtgaggaatt gtgacctgcc cgtttggctt tcgtggcaag tggccaaggc    6240
tggtttgaag acgaatgatc gtaagtggtg ttttgaaggc cctgaggaac atgagatctt    6300
gaatgacagc ggtgaaacag tgaagtgcag ggctcctgga ggagcaaaga agcctctgcg    6360
cccaaggtgg tgtgatgaaa gggtgtcatc tgaccagagt gcgctgtctg aatttattaa    6420
gtttgctgaa ggtaggaggg gagctgctga agtgctagtt gtgctgagtg aactccctga    6480
tttcctggct aaaaaaggtg gagaggcaat ggataccatc agtgtgttcc tccactctga    6540
ggaaggctct agggcttacc gcaatgcact atcaatgatg cctgaggcaa tgacaatagt    6600
catgctgttt atactggctg gactactgac atcgggaatg gtcatctttt tcatgtctcc    6660
caaaggcatc agtagaatgt ctatggcgat gggcacaatg gccggctgtg atatctcat     6720 gttccttgga ggcgtcaaac ccactcacat ctcctatgtc atgctcatat tctttgtcct    6780
gatggtggtt gtgatccccg agccagggca acaaaggtcc atccaagaca accaagtggc    6840
atacctcatt attggcatcc tgacgctggt ttcagcggtg cagccaacg agctaggcat     6900 gctggagaaa accaaagagg acctctttgg gaagaagaac ttaattccat ctagtgcttc    6960
accctggagt tggccggatc ttgacctgaa gccaggagct gcctggacag tgtacgttgg    7020
cattgttaca atgctctctc caatgttgca ccactggatc aaagtcgaat atggcaacct    7080
gtctctgtct ggaatagccc agtcagcctc agtcctttct ttcatggaca agggggatacc   7140 attcatgaag atgaatatct cggtcataat gctgctggtc agtggctgga attcaataac    7200
agtgatgcct ctgctctgtg gcataggggtg cgccatgctc cactggtctc tcattttacc   7260
tggaatcaaa gcgcagcagt caaagcttgc acagagaagg gtgttccatg gcgttgccga    7320
gaaccctgtg gttgatggga atccaacagt tgacattgag gaagctcctg aaatgcctgc    7380
cctttatgag aagaaactgg ctctatatct ccttcttgct ctcagcctag cttctgttgc    7440
catgtgcaga acgcccttt cattggctga aggcattgtc ctagcatcag ctgccttagg    7500
gccgctcata gagggaaaca ccagccttct ttggaatgga cccatggctg tctccatgac    7560
aggagtcatg aggggggaatc actatgcttt tgtgggagtc atgtacaatc tatggaagat    7620
gaaaactgga cgccggggga gcgcgaatgg aaaaactttg ggtgaagtct ggaagaggga    7680
actgaatctg ttgacaagc gacagtttga gttgtataaa aggaccgaca ttgtggaggt    7740
ggatcgtgat acggcacgca ggcatttggc cgaaggggaag gtggcacccg gggtggcggt    7800 ctccagggg accgcaaagt taaggtggtt ccatgagcgt ggctatgtca agctggaagg    7860
tagggtgatt gacctgggggt gtggccgcgg aggctggtgt tactacgctg ctgcgcaaaa    7920
ggaagtgagt ggggtcaaag gatttactct tggaagagac ggccatgaga aacccatgaa    7980
tgtgcaaagt ctgggatgga acatcatcac cttcaaggac aaaactgata tccaccgcct    8040
agaaccagta aaatgtgaca ccctttttgtg tgacattgga gagtcatcat cgtcatcggt    8100
cacagagggg gaaaggaccg tgagagttct tgatactgta gaaaaatggc tggcttgtgg    8160
```

```
ggttgacaac ttctgtgtga aggtgttagc tccatacatg ccagatgttc tcgagaaact   8220
ggaattgctc caaaggaggt ttggcggaac agtgatcagg aaccctctct ccaggaattc   8280
cactcatgaa atgtactacg tgtctggagc ccgcagcaat gtcacattta ctgtgaacca   8340
aacatcccgc ctcctgatga ggagaatgag gcgtccaact ggaaaagtga ccctggaggc   8400
tgacgtcatc ctcccaattg ggacacgcag tgttgagaca gacaagggac ccctggacaa   8460
agaggccata gaagaaaggg ttgagaggat aaaatctgag tacatgacct cttggtttta   8520
tgacaatgac aaccCctaca ggacctggca ctactgtggc tcctatgtca caaaaacctc   8580
aggaagtgcg gcgagcatgg taaatggtgt tattaaaatt ctgacatatc catgggacag   8640
gatagaggag gtcacaagaa tggcaatgac tgacacaacc ccttttggac agcaaagagt   8700
gtttaaagaa aaagttgaca ccagagcaaa ggatccacca gcgggaacta ggaagatcat   8760
gaaagttgtc aacaggtggc tgttccgcca cctggccaga gaaaagaacc ccagactgtg   8820
cacaaaggaa gaatttattg caaaagtccg aagtcatgca gccattggag cttacctgga   8880
agaacaagaa cagtggaaga ctgccaatga ggctgtccaa gacccaaagt tctgggaact   8940
ggtggatgaa gaaaggaagc tgcaccaaca aggcaggtgt cggacttgtg tgtacaacat   9000
gatggggaaa agagagaaga agctgtcaga gtttgggaaa gcaaagggaa gccgtgccat   9060
atggtatatg tggctgggag cgcggtatct tgagtttgag gccctgggat tcctgaatga   9120
ggaccattgg gcttccaggg aaaactcagg aggaggagtg gaaggcattg gcttacaata   9180
cctaggatat gtgatcagag acctggctgc aatggatggt ggtggattct acgcggatga   9240
caccgctgga tgggacacgc gcatcacaga ggcagacctt gatgatgaac aggagatctt   9300
gaactacatg agcccacatc acaaaaaact ggcacaagca gtgatggaaa tgacatacaa   9360
gaacaaagtg gtgaaagtgt tgagaccagc cccaggaggg aaagcctaca tggatgtcat   9420
aagtcgacga gaccagagag gatccgggca ggtagtgact tatgctctga acaccatcac   9480
caacttgaaa gtccaattga tcagaatggc agaagcagag atggtgatac atcaccaaca   9540
tgttcaagat tgtgatgaat cagttctgac caggctggag gcatggctca ctgagcacgg   9600
atgtgacaga ctgaagagga tggcggtgag tggagacgac tgtgtggtcc ggcccatcga   9660
tgacaggttc ggcctggccc tgtcccatct caacgccatg tccaaggtta gaaaggacat   9720
atctgaatgg cagccatcaa agggtggaa tgattgggag aatgtgccct tctgttccca   9780
ccacttccat gaactacagc tgaaggatgg caggaggatt gtggtgcctt gccgagaaca   9840
ggacgagctc attgggagag aagggtgtc tccaggaaac ggctggatga tcaaggaaac   9900
agcttgcctc agcaaagcct atgccaacat gtggtcactg atgtattttc acaaaaggga   9960
catgaggcta ctgtcattgg ctgtttcctc agctgttccc acctcatggg ttccacaagg  10020
acgcacaaca tggtcgattc atgggaaagg ggagtggatg accacggaag acatgcttga  10080
ggtgtggaac agagtatgga taccaacaa cccacacatg caggacaaga caatggtgaa  10140
aaaatggaga gatgtccctt atctaaccaa gagacaagac aagctgtgcg gatcactgat  10200
tggaatgacc aatagggcca cctgggccct ccacatccat ttagtcatcc atcgtatccg  10260
aacgctgatt ggacaggaga atacactga ctacctaaca gtcatggaca ggtattctgt  10320
ggatgctgac ctgcaactgg gtgagcttat ctgaaacacc atctaacagg aataaccggg  10380 atacaaaccga cgggtggaga accggactcc ccacaacctg aaaccgggat ataaaccacg  10440 gctgagaac cgggctccgc acttaaaatg aaacagaaac cgggataaaa actacgatg  10500 gagaaccgga ctccacacat tgagacagaa gaagttgtca gcccagaacc ccacacgagt  10560
```

-continued

```
tttgccactg ctaagctgtg aggcagtgca ggctgggaca gccgacctcc aggttgcgaa  10620
aaacctggtt tctgggacct cccaccccag agtaaaaaga acggagcctc cgctaccacc  10680
ctcccacgtg gtggtagaaa gacggggtct agaggttaga ggagaccctc cagggaacaa  10740
atagtgggac catattgacg ccagggaaag accggagtgg ttctctgctt ttcctccaga  10800
ggtctgtgag cacagtttgc tcaagaataa gcagaccttt ggatgacaaa cacaaaacca  10860
ct                                                                 10862
```

<210> SEQ ID NO 8
<211> LENGTH: 10707
<212> TYPE: DNA
<213> ORGANISM: Dengue virus type 3

<400> SEQUENCE: 8

```
agttgttagt ctacgtggac cgacaagaac agtttcgact cggaagcttg cttaacgtag     60
tgctaacagt tttttattag agagcagatc tctgatgaac aaccaacgga agaagacggg    120
aaaaccgtct atcaatatgc tgaaacgcgt gagaaaccgt gtgtcaactg gatcacagtt    180
ggcgaagaga ttctcaaaag gactgctgaa cggccaggga ccaatgaaat tggttatggc    240
gttcatagct ttcctcagat ttctagccat tccaccaaca gcaggagtct tggctagatg    300
gggaaccttc aagaagtcgg gggccattaa ggtcctgaaa ggcttcaaga aggagatctc    360
aaacatgctg agcataatca acaaacggaa aaagacatcg ctctgtctca tgatgataat    420
gccagcagca cttgctttcc acttgacttc acgagatgga gagccgcgca tgattgtggg    480
gaagaatgaa agaggaaaat ccctactttt taagacagcc tctggaatta acatgtgcac    540
actcatagcc atggacttgg gagagatgtg tgatgacacg gtcacttaca aatgccccca    600
cattaccgaa gtggaacctg aagacattga ctgctggtgc aaccttacat caacatgggt    660
gacttatgga acgtgcaatc aagccggaga gcgtagacgc gacaagagat cagtggcgtt    720
agctccccat gtcggcatgg gactagacac acgcacccaa acctggatgt cggctgaagg    780
agcttggagg caagtcgaga aggtagagac atgggccctt aggcacccag ggttcaccat    840
actagcccta tttcttgccc attacatagg cacatccttg acccagaagg tggttatttt    900
tatactacta atgctggtca ccccatccat gacaatgaga tgtgtgggag taggaaacag    960
agattttgtg gaaggtctat caggagctac gtgggttgac gtggtgctcg agcacggggg   1020
gtgtgtgact accatggcta agaacaagcc aacgttggat atagagcttc agaagaccga   1080
ggccacccaa ttggcgaccc taaggaagct atgcattgag gggaaaatta ccaacataac   1140
aactgactca agatgtccta cccaagggga agcggttttg cctgaggagc aggaccagaa   1200
ctacgtgtgt aagcatacat acgtagacag aggctggggg aacggatgtg gtttgtttgg   1260
caagggaagc ttggtaacat gtgcgaaatt tcaatgcctg gaaccaatag agggaaaagt   1320
ggtgcaatat gagaacctca aatacaccgt catcatcaca gtgcacacag gagatcaaca   1380
ccaggtggga aatgaaacgc agggagtcac ggctgagata acacctcagg catcaaccac   1440
tgaagccatc ttgcctgaat atggaaccct tgggctagaa tgctcaccac ggacaggttt   1500
ggatttcaat gaaatgatct tgctaacaat gaagaacaaa gcatggatgg tacatagaca   1560
atggtttttt gacctacctc taccatggac atcaggagct acaacggaaa caccaacctg   1620
gaacaggaag gagcttcttg tgacatttaa aaacgcacat gcgaaaaaac aagaagtagt   1680
tgtccttgga tcgcaagagg gagcaatgca taccgcattg acaggagcca cagaaatcca   1740
aaactcagga ggcacaagta tttttgcggg gcacttaaaa tgtagactta agatggacaa   1800
```

```
attggaactc aaggggatga gctatgcaat gtgcacgaat acctttgtgt tgaagaaaga    1860
agtctcagaa acgcagcatg ggacaatact cattaaggtc gagtacaaag gggaagatgc    1920
accttgcaag attcctttct ccacagagga tggacaaggg aaagctcaca atggcagact    1980
gattacagcc aacccagtgg tgactaagaa ggaggagcct gtcaatattg aggctgaacc    2040
tcctttgggg gaaagtaata tagtgattgg aattggagac aacgccttga aaatcaactg    2100
gtataagaaa ggaagctcta ttgggaagat gttcgaggcc actgccagag gtgcaaggcg    2160
catggccatc ttgggagaca cagcttggga ctttggatca gtgggtggtg ttctgaactc    2220
attaggcaaa atggtgcacc aaatattcgg aagtgcttac acagccctat tcagtggagt    2280
ctcttgggta tgaaaatcg gaataggagt tctcttgact tggatagggt tgaattcaaa    2340
aaacacatcc atgtcatttt catgcattgc gataggaatc atcacactct atctgggagc    2400
tgtggtgcaa gctgacatgg gatgtgttat aaactggaaa ggcaaagaac tcaaatgtgg    2460
aagtggaatc ttcgtcacca acgaggtcca tacctgggaca gagcaataca aattccaagc    2520
agactcccca aaaagattgg cgacagccat tgcaggcgct tgggagaatg gagtgtgcgg    2580
aattaggtca acaaccagaa tggagaatct cctgtgaaag caaatagcca atgaactgaa    2640
ctacatattg tgggaaaaca atatcaaatt aacggtagtt gtgggcgata taattggggt    2700
cttagagcaa ggaaaaagaa cactaacacc acaacccatg gagctaaaat actcatggaa    2760
aacgtgggga aaggcaaaaa tagtgacagc tgaaacacaa aattcctctt tcataataga    2820
cgggccaaac acgccggagt gtccaagtgc ctcaagagca tggaatgtgt gggaggtgga    2880
agattacggg ttcggagtct tcacaaccaa catatggctg aaactccgag aggtgtacac    2940
ccaactatgt gaccataggc taatgtcggc agctgttaag gatgagaggg ccgtacatgc    3000
cgacatgggc tattggatag aaagccaaaa gaatggaagt tggaagctag aaaaagcatc    3060
cctcatagag gtgaaaacct gcacatggcc aaaatcacat accctttgga gtaatggtgt    3120
gctagagagt gacatgatca tcccaaagag tctagctggt cctatttcgc aacacaacca    3180
caggcccggg taccacaccc agacggcggg accctggcat ttaggaaaat tagagctgga    3240
cttcaactat tgtgaaggaa caacagttgt catcacagaa aactgtggga caagaggccc    3300
atcattgaga caacaacag tgtcaggaaa gttaatacac gaatggtgtt gccgttcgtg    3360
cacacttcct cccttgcgat acatgggaga agacggttgc tggtatggca tggaaatcag    3420
acccatcagt gagaaagaag agaacatggt aaagtcttta gtctcagcgg gaagtggaaa    3480
ggtggacaac ttcacaatgg gtgtcttgtg tttggcaatc ctctttgaag aggtgatgag    3540
aggaaaattt gggaagaaac acatgattgc gggggttttc ttcacgtttg tgctccttct    3600
ctcagggcaa ataacatgga gagacatggc gcacacacta ataatgattg ggtccaacgc    3660
atctgacagg atgggaatgg gcgttaccta cctagcttta attgcaacat ttaaaatcca    3720
gccattcttg gctttgggat ttttcctaag aaaactgaca tccagagaaa atttattgtt    3780
aggagttggg ctggctatgg caacaacgtt acaactgcca gaggacattg aacaaatggc    3840
aaatggaatc gctctggggc tcatggctct taaactgata acacaatttg aaacatacca    3900
attatgacacg gcattaatct ccttaacgtg ttcaaataca atgtttacgt tgactgttgc    3960
ctggagaaca gccaccctga ttttggccgg agtttcgctt ttaccagtgt gccagtcttc    4020
gagcatgagg aaaacagact ggcttccaat ggcagtggca gctatgggag ttccacctct    4080
accactttt atttttagct tgaaagacac acttaaaagg agaagctggc cactgaatga    4140
aggggtgatg gctgttgggc ttgtgagcat tctggccagt tctctcctta gaaatgatgt    4200
```

```
acccatggct ggaccattag tggccggggg cttgctgata gcgtgctacg tcataactgg      4260
cacgtcagca gacctcaccg tagaaaaagc agcagatata acatgggagg aagaggctga      4320
gcaaacagga gtgtcccaca acttaatgat cacagttgat gatgatgaa caatgagaat       4380 aaaagatgat gagactgaga atatcctaac agtgcttttg aaaacagcat tactaatagt     4440
atcaggagtc tttccatact ccatacccgc aacattgctg gtctggcata cttggcaaaa     4500
gcaaacccaa agatccggcg ttctatggga cgtacccagc cccccagaga cacagaaagc     4560
agaactggaa gaaggggtct ataggatcaa acagcaagga atttttggga aaacccaagt     4620
aggggttgga gtacagaaag aaggagtctt ccacaccatg tggcacgtta caagagggc      4680 agtgttgaca tataatggga aaagactgga accgaactgg gctagcgtga aaaaagatct     4740
gatttcatac ggaggaggat ggagattgag cgcacaatgg caaaaggggg aggaggtgca     4800
ggttattgcc gtagagcctg gaagaaccc aaagaacttt caaaccatgc caggcacttt      4860
tcagactaca acagggaaa taggagcaat tgcactggat tcaagcctg gaacttcagg       4920 atctcctatc ataaacagag agggaaaggt agtgggactg tatggcaatg gagtggttac     4980
aaagaatggt ggctacgtca gcggaatagc gcaaacgaat gcagaaccag atggaccgac     5040
accagaattg gaagaagaga tgttcaaaaa gcgaaatcta accataatgg atcttcatcc     5100
tgggtcagga aagacacgga aataccttcc agctattgtt agagaggcaa tcaagagacg     5160
tttaagaact ctaattttgg caccgacaag ggtggttgca gctgagatgg aagaagcatt     5220
gaaagggctc ccaataaggt accaaacaac agcaacaaaa tctgaacaca caggaagaga     5280
gattgttgat ctaatgtgcc acgcaacgtt cacaatgcgt ctgctgtcac cagttagggt     5340
tccaaactat aacttgataa taatggatga agcccatttc acagacccag ccagtatagc     5400
ggctagaggg tacatatcga ctcgtgttgg aatgggagag gcagccgcaa ttttcatgac     5460
agcaacgccc cctggaacag ctgatgcctt tcctcagagc aacgctccaa ttcaagatga     5520
agaaagggac ataccagaac gctcatggaa ttcaggcaat gaatggatta ccgacttcgc     5580
tgggaaaacg gtgtggtttg tccccagcat taaagccgga aatgacatag caaactgctt     5640
gcggaaaaac gggaaaaagg tcattcaact tagtaggaag acttttgaca cagaatatca     5700
gaaaactaaa ctgaatgatt gggacttcgt ggtgacaact gacatttcag aaatgggggc     5760
caatttcaaa gcagatagag tgatcgaccc aagaagatgt ctcaaaccag tgatcctgac     5820
agatggacca gagcgggtga tcctggctgg accaatgcca gtcaccgcgg cgagtgctgc     5880
gcaaaggaga gggagagttg gcaggaaccc acaaaaagaa aatgaccagt acatattcac     5940
gggccagcct ctcaacaatg atgaagacca tgctcactgg acagaagcaa aaatgctgct     6000
ggacaacatt aatacaccag aagggatcat accagctctc tttgagccag aaagggagaa     6060
gtcagccgcc atagcggtg agtatcgctt gaaaggtgag tccaggaaga ctttcgtgga      6120
actcatgagg agggggtgacc ttccagtctg gttagcccat aaagtagcat cagaagggat    6180
caaatataca gatagaaaat ggtgctttga tggacaacgt aataatcaaa ttttagagga     6240
gaacatggat gtggaaatct ggacaaagga aggagaaaag aaaaaattga gacctaggtg    6300
gcttgatgcc cgcacttatt cagatcccctt agcactcaag gaattcaagg actttgcggc   6360
tggcagaaag tcaatcgccc ttgatcttgt gacagaaata ggaagagtgc ttcacacct     6420 agcccataga acgagaaacg ctctggacaa tctggtgatg ctgcatacgt cagaacatgg    6480
cggtagggcc tacaggcatg cggtggagga actaccagac acaatggaaa cactcctact   6540
cttgggactc atgatcttgt tgacaggtgg agcaatgctt ttcttaatat caggtaaagg   6600
```

```
gattggaaag acttcaatag gactcatttg tgtaattgct tccagcggca tgttgtggat    6660
ggccgaaatc ccactccaat ggatcgcgtc ggctatagtc ctggagtttt ttatgatggt    6720
gttgcttata ccagaaccag aaaagcagag aaccccccaa gacaaccaac tcgcatatgt    6780
cgtgataggc atacttacat tggctgcaat aatagcagcc aatgaaatgg gattgttgga    6840
aactacaaag agagatttag gaatgtctaa ggagccaggt gttgtctctc caaccagcta    6900
tttagatgtg gacttgcacc cagcatcagc ctggacattg tacgccgtgg ccactacagt    6960
aataacacca atgttaagac ataccataga gaattctaca gcaaatgtgt ctctggcagc    7020
tatagccaac caggcagtgg tcctgatggg tttggacaaa ggatggccaa tatcaaaaat    7080
ggacttagga gtacccctac tggcattggg ttgctattca caagtgaacc cactgactct    7140
aacagcggca gtactcttgc tgatcacaca ttatgctatt ataggtccag gattgcaggc    7200
aaaagccact cgtgaagctc agaaaaggac agctgctgga ataatgaaga tccaacggt     7260
ggatgggata atgacaatag acctagatcc tgtaatatat gattcaaaat ttgaaaagca    7320
actgggacag ttatgctcc tggttttgtg tgcagttcaa cttttgttaa tgagaacatc     7380
atgggccttg tgtgaagctt taactctagc tacaggacca ataacaacac tctgggaagg    7440
atcacctggg aagttttgga acaccacgat agctgtttcc atggcgaaca tttttagagg    7500
gagctattta gcaggagctg ggcttgcttt ttctattatg aaatcagttg gaacaggaaa    7560
aagaggaaca ggctcacaag gtgaaacctt aggagaaaaa tggaaaaaga aattaaatca    7620
attatcccgg aaaagtttg acctttacaa gaaatctgga atcactgaag tggatagaac    7680
agaagccaaa gaagggttga aaagaggaga ataacacat catgccgtgt ccagaggtag     7740
cgcaaaactt caatggtttg tggagagaaa catggtcatt cccgaaggaa gagtcataga    7800
cttgggctgt ggaagaggag gctggtcata ttactgtgca ggactgaaaa aagtcacaga    7860
agtgcgagga tacacaaaag gcggtccagg acacgaagaa ccagtaccca tgtccacata    7920
tggatggaac atagttaagt taatgagtgg aaaggatgtg ttttatcttc cacctgaaaa    7980
gtgtgacacc ctgttgtgtg acattggaga atcttcacca agcccaacag tggaagaaag    8040
cagaactata gagttttga agatggttga accatggcta aagaacaacc aattttgcat    8100
taaagtattg aacccttaca tgccaactgt gattgagcac ctagaaagac tacaaaggaa    8160
acatggagga atgcttgtga gaaatccact ttcacgaaac tccacgcacg aaatgtactg    8220
gatatctaat ggcacaggta acattgtcgc ttcagtcaat atggtatcta gactgctact    8280
gaacaggttc acgatgacac acagaagacc caccattgag aaagatgtgg atttaggagc    8340
aggaactcga catgttaatg cggaaccaga aacacccaac atggatgtca ttggggaaag    8400
aataaaaagg atcaaggagg agcataattc aacatggcac tatgatgacg aaaaccccta    8460
caaaacgtgg gcttaccatg gatcttatga agtcaaagcc acaggctcag cctcctccat    8520
gataaatgga gtcgtgaaac tcctcactaa accatggat gtggtgccca tggtgacaca     8580
gatggcaatg acagatacaa ctccatttgg ccagcagaga gtctttaaag agaaagtgga    8640
caccaggaca cccaggtcca tgccaggaac aagaagggtc atggggatca cagcggagtg    8700
gctctggaga accctgggaa ggaacaaaaa acccaggtta tgcacaaggg aagagtttac    8760
aaaaaaggtc agaactaacg cagccatggg cgccgttttc acagaggaga ccaatggga    8820
cagcgcgaaa gctgctgttg aggatgagga ttttggaaaa cttgtggaca gagaacgtga    8880
actccacaaa ttgggcaagt gtggaagctg tgtttacaac atgatgggca agagagaaa     8940
gaaacttgga gagtttggca aagcaaaagg cagtagagct atatggtaca tgtggttggg    9000
```

```
agccaggtac cttgagttcg aagcccttgg attcttaaat gaagaccact ggttctcgcg 9060
tgagaactct tacagtggag tggaaggaga aggactgcac aagctaggct atatattaag 9120
ggacatttcc aagatacccg gaggagctat gtatgctgat gacacagctg gttgggacac 9180
aagaataaca gaagatgacc tgcacaatga ggaaaagatc acacagcaaa tggaccctga 9240
acacaggcag ttagcgaacg ctatatttaa gctcacatac caaaacaaag tggtcaaagt 9300
tcaacgaccg actccaacag gcacggtaat ggacatcata tctaggaaag accaaagagg 9360
cagtggacag gtaggaactt atggtctgaa tacattcacc aacatggaag cccagttaat 9420
cagacaaatg gaaggagaag gtgtgctgtc aaaggcagac ctcgagaacc ctcatctgcc 9480
agagaagaaa attacacaat ggttggaaac caaaggagtg gagaggttaa aaagaatggc 9540
cattagcggg gatgattgcg tagtgaaacc aatcgatgac aggttcgcta atgccctgct 9600
cgctctgaac gatatgggga aggttcggaa agacatacct caatggcagc catcaaaggg 9660
atggcatgat tggcaacagg ttcctttctg ctcccaccac tttcatgaat tgatcatgaa 9720
agatggaaga aagttggtgg ttccctgcag accccaggac gaactaatag gaagagcaag 9780
aatctctcaa ggagcgggat ggagccttag agaaaccgca tgtctgggga aagcctacgc 9840
tcaaatgtgg agtctcatgt attttcacag aagagacctc agactagcat ccaacgccat 9900
atgttcagca gtaccagtcc actgggtccc cacaagtaga acgacatggt ctattcatgc 9960
tcaccatcag tggatgacca cagaagacat gcttactgtc tggaacaggg tgtggatcga 10020
ggacaatcca tggatggaag acaaaactcc agtcacaacc tgggaaaatg ttccatatct 10080
agggaagaga gaagaccaat ggtgcggatc acttattggt ctcacttcca gagcaacctg 10140
ggcccagaac atacccacag caattcaaca ggtgagaagc cttataggca atgaagagtt 10200
tctggactac atgccttcaa tgaagagatt taggaaggag gaggagtcgg agggagccat 10260
ttggtaaacg taggaagtga aaaagaggtt aactgtcagg ccacattaag ccacagtacg 10320
gaagaagctg tgctgcctgt gagccccgtc caaggacgtt aaaagaagaa gtcaggcccc 10380
aaagccacgg tttgagcaaa ccgtgctgcc tgtagctccg tcgtggggac gtaaaacctg 10440
ggaggctgca aactgtggaa gctgtacgca cggtgtagca gactagcggt tagaggagac 10500
ccctcccatg acacaacgca gcagcggggc ccgagcactg agggaagctg tacctccttg 10560
caaaggacta gaggttagag gagacccccc gcaaataaaa acagcatatt gacgctggga 10620
gagaccagag atcctgctgt ctcctcagca tcattccagg cacagaacgc cagaaaatgg 10680
aatggtgctg ttgaatcaac aggttct 10707
```

```
<210> SEQ ID NO 9
<211> LENGTH: 10735
<212> TYPE: DNA
<213> ORGANISM: Dengue virus type 1 (LAV1)

<400> SEQUENCE: 9
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
```

```
gcccacagcc ctggcgttcc atctgacgac acgaggggga gagccgcata tgatagttag    480
caagcaggaa agaggaaagt cacttttgtt caagacctct gcaggtgtca acatgtgcac    540
cctcattgcg atggatttgg gagagttgtg tgaggcacg atgacctaca aatgcccccg     600
gatcactgag gcggaaccag atgacgttga ctgttggtgc aatgccacgg acacatgggt    660
gacctatgga acgtgctctc aaactggcga acaccgacga acaaacgtt ccgtcgcatt     720 ggccccacac gtggggcttg gcctagaaac aagagccgaa acgtggatgt cctctgaagg    780
tgcttggaaa cagatacaaa aagtagagac ttgggctctg agacatccag gattcacggt    840
gatagccctt tttctagcac atgccatagg aacatccatc acccagaaag ggatcatttt    900
cattttgctg atgctggtaa caccatctat ggccatgcga tgcgtgggaa taggcaacag    960
agacttcgtg gaaggactgt caggagcaac atgggtggat gtggtactgg agcatggaag   1020
ttgcgtcacc accatggcaa aaaacaaacc aacactggac attgaactct gaagacgga    1080 ggtcacaaac cctgcagttc tgcgtaaatt gtgcattgaa gctaaaatat caaacaccac   1140
caccgattcg agatgtccaa acaaggaga agccacactg gtggaagaac aagacgcgaa    1200 cttttgtgtgc cgacgaacgt tcgtggacag aggctgggc aatggctgtg ggctattcgg    1260
aaaaggtagt ctaataacgt gtgccaagtt taagtgtgtg acaaaactag aaggaaagat   1320
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aaccccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccgaatgg    1980 gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggactc ggttctatag gaggagtgtt    2220
cacgtctatg ggaaaactgg tacaccaggt ttttggaact gcatatggag ttttgttag    2280 cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcattttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga aacatcatg tggaaacaaa tatcaaatga   2640
attgaaccac atcctacttg aaaatgacat gaaatttaca gtggtcgtgg agacgttag    2700 tggaatcttg gcccaaggga aaaaatgat taggccacaa cccatggaac acaaatactc    2760
gtggaaaagc tggggaaaag ctaaaatcat aggagcggat gtacagaaca ccaccttcat   2820
```

```
catcgacggc ccaaacaccc cagaatgccc tgacaatcaa agagcatgga atatttggga    2880
agtagaggac tatggatttg ggattttcac gacaaacata tggttgaaat tgcgtgactc    2940
ctacacccaa gtatgtgacc accggctgat gtcagctgcc attaaggaca gcaaggcagt    3000
ccatgctgac atggggtact ggatagaaag tgaaagaac gagacatgga agttggcgag     3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggccg tggcacctag caagttgga     3240 actagatttc gattttttgtg aaggtaccac agttgttgtg gatgaacatt gtggaaatcg    3300
aggaccatct ctcagaacca caacagtcac aggaaagata tccatgaat ggtgctgcag     3360 atcttgtacg ctacccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccacttcaa    3720 aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta aacagaaaa caaatctgg ggaaggaaga gttggccct     4140 caatgaagga attatggctg ttggaatagt tagtattcta ctaagttcac ttttaaaaaa    4200
tgatgtgccg ctagccggcc cattaatagc tggaggcatg ctaatagcat gttatgtcat    4260
atccggaagc tcagctgatt tatcactgga gaaagcggct gaggtctcct gggaggaaga    4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc aatgtcaat accagcgacc cttttttgtgt ggtattttg     4500 gcagaaaaag aaacagagat caggagtgct atgggacaca cccagccccc cagaagtgga    4560
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag acccctgaag gcgaagttgg agccatagcc ttagactttta aacctggcac    4920 atctggatct cccatcgtaa acagagaggg aaaaatagta ggtctttatg gaaatggagt    4980
ggtgacaaca agcggaactt acgttagtgc catagctcaa gctaaggcat acaagaagg    5040 gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
```

```
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaacgggaa acgggtgatc caattgagca gaaaaacctt tgacactga   5700 gtaccagaaa acaaaaaaca acgactggga ctatgtcgtc acaacagaca tttccgaaat   5760
gggagcaaat ttccgggccg acagggtaat agacccaagg cggtgtctga accggtaat   5820 actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa acaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaatagggaa aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttctttttga   7380
tcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
```

```
actaaaccaa ctgagcaagt cagaattcaa tacttacaag aggagtggga ttatggaggt    7680
ggatagatcc gaagccaaag agggactgaa aagaggagaa acaaccaaac acgcagtatc    7740
gagaggaacg gccaaactga ggtggttcgt ggagaggaac cttgtgaaac cagaagggaa    7800
agtcatagac ctcggttgtg aagaggtgg ctggtcatat tattgcgctg ggctgaagaa     7860
agtcacagaa gtgaaaggat acacaaaagg aggacctgga catgaggaac caatcccaat    7920
ggcgacctat ggatggaacc tagtaaagct gcactccgga aaagatgtat tttttatacc    7980
acctgagaaa tgtgacaccc ttttgtgtga tattggtgag tcctctccga acccaactat    8040
agaggaagga agaacgttac gtgttctgaa aatggtggaa ccatggctca gaggaaacca    8100
attttgcata aaaattctaa atccctatat gccgagcgtg gtagaaactc tggaacaaat    8160
gcaaagaaaa catggaggaa tgctagtgcg aaacccactc tcaagaaatt ccacccatga    8220
aatgtactgg gtttcatgtg aacaggaaa cattgtgtca gcagtaaaca tgacatctag     8280
aatgttgcta atcggttca caatggctca caggaagcca acatatgaaa gagacgtgga     8340
cttaggcgct ggaacaagac atgtggcagt agaaccagag gtagccaacc tagatatcat    8400
tggccagagg atagagaata taaaaaatga acataagtca acatggcatt atgatgagga    8460
caatccatac aaaacatggg cctatcatgg atcatatgag gttaagccat caggatcggc    8520
ctcatccatg gtcaatggcg tggtgagatt gctcaccaaa ccatgggatg ttatccccat    8580
ggtcacacaa atagccatga ctgataccac acccttttgga caacagaggg tgtttaaaga    8640
gaaagttgac acgcgcacac caaaagcaaa acgtggcaca gcacaaatta tggaagtgac    8700
agccaggtgg ttatggggtt tccttttctag aaacaaaaaa cccagaattt gcacaagaga    8760
ggagtttaca agaaaagtta ggtcaaacgc agctattgga gcagtgttcg ttgatgaaaa    8820
tcaatggaac tcggcaaaag aagcagtgga agacgaacgg ttctgggaac ttgtccacag    8880
agagagggag cttcataaac aggggaaatg tgccacgtgt gtctacaata tgatggggaa    8940
gagagagaaa aaattaggag agttcggaaa ggcaaaagga agtcgtgcaa tatggtacat    9000
gtggttggga gcacgcttcc tagagtttga agcccttggt ttcatgaatg aagatcactg    9060
gttcagtaga gagaattcac tcagtggagt ggaaggagaa ggactccaca acttggata     9120 catactcaga gacatatcaa ggattccagg ggggaacatg tatgcagatg acacagccgg    9180
atgggacaca agaataacag aggatgatct ccagaatgag gctaaaatca ctgacatcat    9240
ggagcccgaa catgccctgc tggctacgtc aatctttaag ctgacctacc aaaataaggt    9300
ggtaagggtg cagagaccag caaaaaatgg aaccgtgatg gatgttatat ccagacgtga    9360
ccagagaggc agtggacagg ttggaactta tggcttaaac actttcacca acatggaggc    9420
ccaactgata agacaaatgg agtctgaggg aatcttttta cccagcgaat ggaaaccccc    9480
aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtatttt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga ataggggtctg   10020
```

```
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
gctccatcgt ggggatgtaa aaacccggga ggctgcaacc catggaagct gtacgcatgg  10500
ggtagcagac tagtggttag aggagacccc tcccaagaca caacgcagca gcggggccca  10560
acaccagggg aagctgtacc ctggtggtaa ggactagagg ttagaggaga cccccgcgt  10620
aacaataaac agcatattga cgctgggaga gaccagagat cctgctgtct ctacagcatc  10680
attccaggca cagaacgcca gaaaatggaa tggtgctgtt gaatcaacag gttct       10735
```

<210> SEQ ID NO 10
<211> LENGTH: 10723
<212> TYPE: DNA
<213> ORGANISM: Dengue virus type 2 (LAV2)

<400> SEQUENCE: 10

```
agttgttagt ctacgtggac cgacaaagac agattctttg agggagctaa gctcaatgta     60
gttctaacag tttttttaatt agagagcaga tctctgatga ataaccaacg gaaaaaggcg    120
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggttggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acacgaactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatgc gttgcatagg aatgtcaaat    960
agagactttg tggaaggggt ttcaggagga agctgggttg acatagtctt agaacatgga   1020
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
```

```
tccatcacag aagcagaatt gacaggttat ggcactgtca caatggagtg ctctccaaga    1500
acgggcctcg acttcaatga gatggtgttg ctgcagatgg aaaataaagc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgtcatcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat cccttttgag ataatggatt tggaaaaaag acatgtctta    1980
ggtcgcctga ttacagtcaa cccaattgtg acagaaaaag atagcccagt caacatagaa    2040
gcagaacctc catttggaga cagctacatc atcataggag tagagccggg acaactgaag    2100
ctcaactggt ttaagaaagg aagttctatc ggccaaatgt tgagacaac aatgaggggg    2160 gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ctagtattgg tgggaattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagaggac    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggctaaa attgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctgagc    3120 aatggagtgc tagaaagtga gatgataatt ccaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300 agaggacccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaagaagag aatttggtca actccttggt cacagctgga    3480
catgggcagg tcgacaactt ttcactagga gtcttggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcgacc aactttttgc agctggacta ctcttgagaa agctgacctc caaggaattg    3780
atgatgacta ctataggaat tgtactcctc tcccagagca ccataccaga gaccattctt    3840
```

```
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttct aacaaccctc tcaagaacca gcaagaaaag gagctggcca     4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactggaaga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac catcatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca acgaaacct    4860
ggtcttttca aaaccaacgc cggaacaata ggtgctgtat ctctggactt ttctcctgga    4920
acgtcaggat ctccaattat cgacaaaaaa ggaaaagttg tgggtctttat tggtaatggt     4980
gttgttacaa ggagtggagc atatgtgagt gctatagccc agactgaaaa aagcattgaa    5040
gacaacccag agatcgaaga tgacatttttc cgaaagagaa gactgaccat catggaccctc    5100
cacccaggag cgggaaagac gaagagatac cttccggcca tagtcagaga agctataaaa    5160
cggggtttga gaacattaat cttggccccc actagagttg tggcagctga atggaggaa    5220
gcccttagag gacttccaat aagataccag accccagcca tcagagctgw gcacaccggg    5280
cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggatttt    5460
atgacagcca ctccccgggg aagcagagac ccatttcctc agagcaatgc accaatcata    5520
gatgaagaaa gagaaatccc tgaacgctcg tggaattccg acatgaatg ggtcacggat     5580
tttaaaggga gactgttttg gttcgttcca agtataaaag caggaaatga tatagcagct    5640
tgcctgagga aaaatggaaa gaaagtgata caactcagta ggaagacctt tgattctgag    5700
tatgtcaaga ctagaaccaa tgattgggac ttcgtggtta caactgacat ttcagaaatg    5760
ggtgccaatt tcaaggctga gagggttata gaccccagac gctgcatgaa accagtcata    5820
ctaacgatg tgtgaagagcg ggtgattctg gcaggaccta tgccagtgac ccactctagt    5880
gcagcacaaa gaagagggag aataggaaga aatccaaaaa atgagaatga ccagtacata    5940
tacatggggg aacctctgga aaatgatgaa gactgtgcac actggaaaga agctaaaatg    6000
ctcctagata acatcaacac gccagaagga atcattccta gcatgttcga accagagcgt    6060
gaaaaggtgg atgccattga tggcgaatac cgcttgagag gagaagcaag gaaaaccttt    6120
gtagacttaa tgagaagagg agaccctacca gtctggttgg cctacagagt ggcagctgaa    6180
ggcatcaact acgcagacag aaggtggtgt tttgatggag tcaagaacaa ccaaatccta    6240
```

```
gaagaaaacg tggaagttga aatctggaca aaagaagggg aaaggaagaa attgaaaccc    6300
agatggttgg atgctaggat ctattctgac ccactggcgc taaaagaatt taaggaattt    6360
gcagccggaa gaaagtctct gaccctgaac ctaatcacag aaatgggtag gctcccaacc    6420
ttcatgactc agaaggcaag agacgcactg gacaacttag cagtgctgca cacggctgag    6480
gcaggtggaa gggcgtacaa ccatgctctc agtgaactgc cggagaccct ggagacattg    6540
cttttactga cacttctggc tacagtcacg ggagggatct ttttattctt gatgagcgca    6600
aggggcatag ggaagatgac cctgggaatg tgctgcataa tcacggctag catcctccta    6660
tggtacgcac aaatacagcc acactggata gcagcttcaa taatactgga gttttttctc    6720
atagttttgc ttattccaga acctgaaaaa cagagaacac cccaagacaa ccaactgacc    6780
tacgttgtca tagccatcct cacagtggtg gccgcaacca tggcaaacga gatgggtttc    6840
ctagaaaaaa cgaagaaaga tctcggattg gaagcattg caacccagca acccgagagc    6900
aacatcctgg acatagatct acgtcctgca tcagcatgga cgctgtatgc cgtggccaca    6960
acatttgtta caccaatgtt gagacatagc attgaaaatt cctcagtgaa tgtgtcccta    7020
acagctatag ccaaccaagc cacagtgtta atgggtctcg ggaaaggatg gccattgtca    7080
aagatggaca tcggagttcc ccttctcgcc attggatgct actcacaagt caaccccata    7140
actctcacag cagctcttt cttattggta gcacattatg ccatcatagg gccaggactc    7200
caagcaaaag caaccagaga agctcagaaa agagcagcgg cgggcatcat gaaaaaccca    7260
actgtcgatg gaataacagt gattgaccta gatccaatac cttatgatcc aaagtttgaa    7320
aagcagttgg acaagtaat gctcctagtc ctctgcgtga ctcaagtatt gatgatgagg    7380
actacatggg ctctgtgtga ggctttaacc ttagctaccg ggcccatctc cacattgtgg    7440
gaaggaaatc cagggaggtt ttggaacact accattgcgg tgtcaatggc taacatttt    7500 agagggagtt acttggccgg agctggactt ctcttttcta ttatgaagaa cacaaccaac    7560
acaagaaggg gaactggcaa cataggagag acgcttggag agaaatggaa aagccgattg    7620
aacgcattgg gaaaagtga attccagatc tacaagaaaa gtggaatcca ggaagtggat    7680
agaaccttag caaaagaagg cattaaaaga ggagaaacgg accatcacgc tgtgtcgcga    7740
ggctcagcaa aactgagatg gttcgttgag agaaacatgg tcacaccaga agggaaagta    7800
gtggacctcg gttgtggcag aggaggctgg tcatactatt gtggaggact aaagaatgta    7860
agagaagtca aaggcctaac aaaaggagga ccaggacacg aagaacccat ccccatgtca    7920
acatatgggt ggaatctagt gcgtcttcaa agtggagttg acgttttctt catcccgcca    7980
gaaaagtgtg acacattat gtgtgacata ggggagtcat caccaaatcc cacagtggaa    8040
gcaggacgaa cactcagagt ccttaactta gtagaaaatt ggttgaacaa caacactcaa    8100
ttttgcataa aggttctcaa cccatatatg ccctcagtca tagaaaaaat ggaagcacta    8160
caaaggaaat atgaggagc cttagtgagg aatccactct cacgaaactc cacacatgag    8220
atgtactggg tatccaatgc ttccgggaac atagtgtcat cagtgaacat gatttcaagg    8280
atgttgatca acagatttac aatgagatac aagaaagcca cttacgagcc ggatgttgac    8340
ctcggaagcg gaacccgtaa catcgggatt gaaagtgaga taccaaaccct agatataatt    8400 gggaaaagaa tagaaaaaat aaagcaagag catgaaacat catggcacta tgaccaagac    8460
cacccataca aaacgtgggc ataccatggt agctatgaaa caaaacagac tggatcagca    8520
tcatccatgt caacggagt ggtcaggctg ctgacaaaac cttgggacgt tgtccccatg    8580
gtgacacaga tggcaatgac agacacgact ccatttggac aacagcgcgt ttttaaagag    8640
```

| | |
|---|---|
| aaagtggaca cgagaaccca agaaccgaaa gaaggcacga agaaactaat gaaaataaca | 8700 |
| gcagagtggc tttggaaaga attagggaag aaaaagacac ccaggatgtg caccagagaa | 8760 |
| gaattcacaa gaaaggtgag aagcaatgca gccttggggg ccatattcac tgatgagaac | 8820 |
| aagtggaagt cggcacgtga ggctgttgaa gatagtaggt tttgggagct ggttgacaag | 8880 |
| gaaaggaatc tccatcttga aggaaagtgt gaaacatgtg tgtacaacat gatgggaaaa | 8940 |
| agagagaaga agctagggga attcggcaag gcaaaaggca gcagagccat atggtacatg | 9000 |
| tggcttggag cacgcttctt agagtttgaa gccctaggat tcttaaatga agatcactgg | 9060 |
| ttctccagag agaactccct gagtggagtg gaaggagaag ggctgcacaa gctaggttac | 9120 |
| attctaagag acgtgagcaa gaaagaggga ggagcaatgt atgccgatga caccgcagga | 9180 |
| tgggatacaa gaatcacact agaagaccta aaaaatgaag aaatggtaac aaaccacatg | 9240 |
| gaaggagaac acaagaaact agccgaggcc attttcaaac taacgtacca aaacaaggtg | 9300 |
| gtgcgtgtgc aaagaccaac accaagaggc acagtaatgg acatcatatc gagaagagac | 9360 |
| caaagaggta gtggacaagt tggcacctat ggactcaata cttttcaccaa tatggaagcc | 9420 |
| caactaatca gacagatgga gggagaagga gtctttaaaa gcattcagca cctaacaatc | 9480 |
| acagaagaaa tcgctgtgca aaactggtta gcaagagtgg ggcgcgaaag gttatcaaga | 9540 |
| atggccatca gtgagatga ttgtgttgtg aaacctttag atgacaggtt cgcaagcgct | 9600 |
| ttaacagctc taaatgacat gggaaagatt aggaaagaca tacaacaatg gaaaccttca | 9660 |
| agaggatgga atgattggac acaagtgccc ttctgttcac accatttcca tgagttaatc | 9720 |
| atgaaagacg gtcgcgtact cgttgttcca tgtagaaacc aagatgaact gattggcaga | 9780 |
| gcccgaatct cccaaggagc agggtggtct ttgcgggaga cggcctgttt ggggaagtct | 9840 |
| tacgcccaaa tgtggagctt gatgtacttc cacagacgcg acctcaggct ggcggcaaat | 9900 |
| gctatttgct cggcagtacc atcacattgg gttccaacaa gtcgaacaac ctggtccata | 9960 |
| catgctaaac atgaatggat gacaacggaa gacatgctga cagtctggaa cagggtgtgg | 10020 |
| attcaagaaa acccatggat ggaagacaaa actccagtgg aatcatggga ggaaatccca | 10080 |
| tacttgggga aaagagaaga ccaatggtgc ggctcattga ttgggttaac aagcagggcc | 10140 |
| acctgggcaa gaacatcca agcagcaata aatcaagtta gatcccttat aggcaatgaa | 10200 |
| gaatacacag attacatgcc atccatgaaa agattcagaa gagaagagga agaagcagga | 10260 |
| gttctgtggt agaaagcaaa actaacatga acaaggcta gaagtcaggt cggattaagc | 10320 |
| catagtacgg aaaaaactat gctacctgtg agccccgtcc aaggacgtta aaagaagtca | 10380 |
| ggccatcata aatgccatag cttgagtaaa ctatgcagcc tgtagctcca cctgagaagg | 10440 |
| tgtaaaaaat ccgggaggcc acaaaccatg gaagctgtac gcatggcgta gtggactagc | 10500 |
| ggttagagga gaccccctccc ttacaaatcg cagcaacaat gggggcccaa ggcgagatga | 10560 |
| agctgtagtc tcgctggaag gactagaggt tagaggagac cccccgaaa caaaaaacag | 10620 |
| catattgacg ctgggaaaga ccagagatcc tgctgtctcc tcagcatcat tccaggcaca | 10680 |
| gaacgccaga aaatggaatg gtgctgttga atcaacaggt tct | 10723 |

<210> SEQ ID NO 11
<211> LENGTH: 10699
<212> TYPE: DNA
<213> ORGANISM: Dengue virus type 3 (LAV3)

<400> SEQUENCE: 11

| | |
|---|---|
| agttgttagt ctacgtggac cgacaagaac agtttcgact cggaagcttg cttaacgtag | 60 |

```
tgctgacagt tttttattag agagcagatc tctgatgaac aaccaacgga aaaagacggg    120
aaaaccgtct atcaatatgc tgaaacgcgt gagaaaccgt gtgtcaactg gatcacagtt    180
ggcgaagaga ttctcaagag gattgctgaa cggccaagga ccaatgaaat tggttatggc    240
atttatagct ttcctcagat ttctagccat tccaccgaca gcaggagtct tggctagatg    300
gggtaccttt aagaagtcgg gggctattaa ggtcttaaaa ggcttcaaga aggagatctc    360
aaacatgctg agcattatca acaaacggaa aaagacatcg ctctgtctca tgatgatgtt    420
accagcaaca cttgctttcc acttaacttc acgagatgga gagccgcgca tgattgtggg    480
gaagaatgaa agaggaaaat ccctactttt caagacagcc tctggaatca acatgtgcac    540
actcatagct atggatctgg gagagatgtg tgatgacacg gtcacttaca aatgccccca    600
cattaccgaa gtggagcctg aagacattga ctgctggtgc aaccttacat cgacatgggt    660
gacttatgga acatgcaatc aagctggaga gcatagacgc gataagagat cagtggcgtt    720
agctccccat gttggcatgg gactggacac acgcactcaa acctggatgt cggctgaagg    780
agcttggaga caagtcgaga aggtagagac atgggcccct aggcacccag ggtttaccat    840
actagcccta tttcttgccc attacatagg cacttccttg acccagaaag tggttatttt    900
tatactatta atgctggtta ccccatccat gacaatgaga tgtgtaggag taggaaacag    960
agattttgtg gaaggcctat cgggagctac gtgggttgac gtggtgctcg agcacggtgg   1020
gtgtgtgact accatggcta agaacaagcc cacgctggac atagagcttc agaagaccga   1080
ggccacccaa ctggcgaccc taaggaagct atgcattgag ggaaaaatta ccaacataac   1140
aaccgactca agatgtccca cccaagggga agcgatttta cctgaggagc aggaccagaa   1200
ctacgtgtgt aagcatacat acgtggacag aggctgggga aacggttgtg gtttgtttgg   1260
caagggaagc ttggtgacat gcgcgaaatt tcaatgttta gaatcaatag agggaaaagt   1320
ggtgcaacat gagaacctca atacaccgt catcatcaca gtgcacacag agaccaaca    1380 ccaggtggga aatgaaacgc agggagtcac ggctgagata acaccccagg catcaaccgc   1440
tgaagccatt ttacctgaat atggaaccct cgggctagaa tgctcaccac ggacaggttt   1500
ggatttcaat gaaatgatct yattgacaat gaagaacaaa gcatggatgg tacatagaca   1560
atggttcttt gacttacccc taccatggac atcaggagct acagcagaaa caccaacttg   1620
gaacaggaaa gagcttcttg tgacatttaa aaatgcacat gcaaaaaagc aagaagtagt   1680
tgttcttgga tcacaagagg gagcaatgca tacagcactg acaggagcta cagagatcca   1740 aaccctcagga ggcacaagta tctttgcggg gcacttaaaa tgtagactca agatggacaa   1800
attggaactc aaagggatga gctatgcaat gtgcttgggt agctttgtgt tgaagaaaga   1860
agtctccgaa acgcagcatg ggacaatact cattaaggtt gagtacaaag ggaaagatgc   1920
accctgcaag attccttttct ccacggagga tggacaagga aaagctcaca atggcagact   1980
gatcacagcc aatccagtgg tgaccaagaa ggaggagcct gtcaacattg aggctgaacc   2040
tccttttgga gaaagtaaca tagtaattgg aattggagac aaagccctga aaatcaactg   2100
gtacaagaag ggaagctcga ttgggaagat gttcgaggct actgccagag gtgcaaggcg   2160
catggccatc ttgggagaca cagcctggga ctttggatca gtgggtggtg ttttgaattc   2220
attagggaaa atggtccacc aaatatttgg agtgcttac acagcccat ttggtggagt   2280 ctcctggatg atgaaaattg gaataggtgt cctcttaacc tggatagggt tgaactcaaa   2340
aaatacttct atgtcatttt catgcatcgc gataggaatc attacactct atctgggagc   2400
cgtggtgcaa gctgacatgg ggtgtgtcat aaactggaaa ggcaaagaac tcaaatgtgg   2460
```

```
aagtggaatt tcgtcactga atgaggtcca cacctggaca gagcaatacg aattttcaagc   2520
agactccccc aagagactgg caacagccat tgcaggcgct tgggaaaatg gagtgtgcgg   2580
aattaggtca acaaccagaa tggagaacct cttgtggaag caaatagcca atgaactgaa   2640
ttacatatta tgggaaaaca acattaaatt aacggtagtt gtaggcgaca taactggggt   2700
cttagagcaa gggaaaagaa cactaacacc acaacccatg gagctaaaat attcttggaa   2760
aacatgggga aaggcaaaaa tagtgacagc tgaaacacaa aattcctctt tcataataga   2820
tgggccaagc acaccggagt gtccaagtgc ctcaagagca tggaatgtgt gggaggtgga   2880
ggattacggg ttcggagttt tcacaaccaa catatggctg aaactccgag aggtgtacac   2940
ccaactatgt gaccataggc taatgtcggc agccgtcaag gatgagaggg ctgtacatgc   3000
cgacatgggc tattggatag aaagccaaaa gaatgggagt tggaagctag aaaaagcatc   3060
cttcatagag gtgaaaacct gcacatggcc aaaatcacac actctctgga gcaatggtgt   3120
gctagagagt gacatgatta tcccaaagag tctagctggt cccatttcgc aacacaacca   3180
caggcccggg taccacaccc aaacggcagg accctggcac ttaggaaaat tggagctgga   3240
cttcaactat tgtgaaggaa caacagttgt catctcagaa actgtgggaa caagaggccc   3300
atcattgaga acaacaacgg tgtcagggaa gttgatacac gaatggtgct gccgctcgtg   3360
cacacttcct cccctacgat acatgggaga agacggctgc tggtatgcca tggaaatcag   3420
acccattaat gagaaagaag agaatatggt aaagtctcta gcctcagcag ggagtggaaa   3480
ggtggacaac ttcacaatgg gtgtcttgtg tttggcaatc ctctttgaag aggtgatgag   3540
aggaaaattt gggaaaaaac acatgattgc aggggttctc ttcacgtttg tgctcctcct   3600
ctcagggcaa ataacatgga gagacatggc gcacacactc ataatgattg ggtccaacgc   3660
ctctgacaga atggggatgg gcgtcactta cctagctcta attgcaacat ttaaaattca   3720
gccactcctg gctttgggat tcttcctgag gaaactgaca tctagagaaa atttattgct   3780
gggagttggg ttggccatgg cagcaacgtt acgactgcca gaggacattg aacagatggc   3840
gaatggaatt gctttgggcc tcatggctct taaactgata acacaatttg aaacatacca   3900
actatggacg gcattagttt ccctaacgtg ttcaaataca attttcacgt tgactgttgc   3960
ctggagaaca gccactctga tttagccgg aatttcgctt ttgccagtgt gccagtcttc   4020
gagcatgagg aaaacagatt ggctcccaat gactgtggca gctatgggag ctcaaccct   4080
accactttt attttcagtc tgaaagatac actcaaaagg agaagctggc cactgaatga   4140
gggggtgatg gcagttggac ttgtgagcat tctagctagt tctctcctta ggaatgatgt   4200
gcctatggct ggaccattag tggctggggg cttgctgata gcgtgctacg tcataactgg   4260
cacgtcagca gacctcactg tagaaaaagc agcagatgta acatgggagg aagaggccga   4320
gcaaacagga gtgtcccaca atttaatggt cacagttgat gatgatgaa caatgagaat   4380
aaaagatgac gagactgaga acatcttaac agtgcttta aaaacagcac tactaatagt   4440
atcaggcatc tttccatact ccatacccgc aacactgttg gtctggcata cttggcaaaa   4500
gcaaacccaa agatccggcg tcctatggga cgtacccagc cccccagaga cacagaaagc   4560
ggaactggaa gaagggggtct ataggatcaa acagcaagga atttttggaa aacccaagt   4620
gggggttgga gtacagaaag aaggagtttt ccacaccatg tggcatgtca agagggggc   4680
agtgttgaca cacaatggga aaagactgga accaaactgg gctagcgtga aaaagatct   4740
gatttcatac ggaggaggat ggagattgag tgcacaatgg aaaagggggg aggaggtgca   4800
ggttattgcc gtagagcctg ggaagaaccc aaagaacttt caaaccatgc caggcattt   4860
```

```
tcagacaaca acaggggaaa taggagcaat tgcactggat ttcaagcctg gaacttcagg    4920
atctcccatc ataaacagag agggaaaggt agtgggactg tatggcaatg gagtggttac    4980
aaagaatgga ggctatgtca gtggaatagc gcaaacaaat gcagaaccag atggaccgac    5040
accagagttg gaagaagaga tgttcaaaaa gcgaaatcta accataatgg atctccatcc    5100
tgggtcagga aagacgcgga aatatcttcc agctattgtt agagaggcaa tcaagagacg    5160
cttaaggact ctaattttgg caccaacaag ggtagttgca gctgagatgg aagaagcatt    5220
gaaagggctc ccaataaggt atcaaacaac tgcaacaaaa tctgaacaca caggaagaga    5280
gattgttgat ctaatgtgtc acgcaacgtt cacaatgcgc ttgctgtcac cagtcagggt    5340
tccaaactac aacttgataa taatggatga ggcccatttc acagaccag ccagtatagc     5400
ggctagaggg tacatatcaa ctcgtgtagg aatgggagag cagccgcaa ttttcatgac     5460
agcaacaccc cctggaacag ctgatgcctt cctcagagc aacgctccaa ttcaagatga     5520
agagagagac ataccggaac gctcatggaa ttcaggcaat gaatggatta ctgactttgt    5580
tgggaagaca gtgtggtttg tccctagcat caaagccgga aatgacatag caaactgctt    5640
gcggaaaaat ggaaaaaagg ttattcaact cagcaggaag acctttgaca cagaatatca    5700
aaagaccaaa ctgaatgatt gggactttgt ggtgacaaca gacatttcag aaatgggagc    5760
caatttcaaa gcagatagag tgatcgaccc aagaagatgt ctcaagccgg tgattttgac    5820
agatggaccc gagcgggtga tcctggctgg accaatgcca gtcaccgtag cgagcgctgc    5880
gcaaaggaga gggagagttg gcaggaaccc acaaaaagaa aatgaccagt acatattcat    5940
gggccagcct ctcaacaatg atgaagacca tgctcactgg acagaagcaa aaatgctgct    6000
ggacaacatc aacacaccag aagggattat accagctctc tttgaaccag aaagggagaa    6060
gtcagccgcc atagacggcg aataccgcct gaagggtgag tccaggaaga ctttcgtgga    6120
actcatgagg aggggtgacc tcccagtttg gctagcccat aaagtagcat cagaagggat    6180
caaatataca gatagaaaat ggtgctttga tggagaacgt aataatcaaa ttttagagga    6240
gaatatggat gtgaaatct ggacaaagga aggagaaaag aaaaaactga gacctaggtg     6300
gcttgatgcc cgcacttatt cagatcctt agcactcaaa gaattcaagg attttgcagc     6360
tggcagaaag tcaatcgccc ttgatcttgt gacagaaata ggaagagtgc ttcacactt     6420
agcccacaga acgagaaacg ccctggataa tttggtgatg ctgcacacgt cagaacatgg    6480
cggtagggcc tacaggcatg cagtggagga actaccagaa acgatggaaa cactcttact    6540
cctgggactg atgatcttgt taacaggtgg agcaatgctc ttcttgatat caggtaaagg    6600
gattggaaag acttcaatag gactcatttg tgtaattgct tccagcggca tgttatggat    6660
ggctgatgtc ccactccaat ggatcgcatc ggctatagtc ctggagttttt ttatgatggt   6720
gttgctcata ccagaaccag aaaagcagag aactccccaa gacaaccaac tcgcatatgt    6780
cgtgataggc atacttacat tggctgcaat agtagcggcc aatgaaatgg gactgttgga    6840
aactacaaag agagatttag gaatgtctaa agaaccaggt gttgtttctc caaccagcta    6900
tttggatgtg gacttgcacc cagcatcagc ctggacattg tacgccgtgg ccacaacagt    6960
aataacacca atgttgagac acaccataga gaattccaca gcaaatgtgt ctctggcagc    7020
catagctaac caggcagtgg tcctgatggg tttagacaaa ggatggccga tatcgaaaat    7080
ggacttgggc gtaccactat tggcactggg ttgctattca caagtgaacc cactaactct    7140
tgcagcggca gtactttttg ctagtcacaca ttatgcaatt ataggtccag gattgcaggc    7200
aaaagccacc cgtgaagctc agaaaaggac agctgctgga ataatgaaga atccaacggt    7260
```

```
ggatggaata atgacaatag acctagatcc tgtaatatat gattcaaaat ttgaaaagca    7320
actaggacag gtcatgctcc tggttctgtg tgcagtccaa cttttattga tgagaacatc    7380
atgggccttg tgtgaagttc taaccctagc cacaggacca ataacaacac tctgggaagg    7440
atcacctggg aagttctgga acaccacgat agctgtttcc atggcgaaca tctttagagg    7500
gagctattta gcaggagctg ggcttgcttt ttctatcatg aaatcagttg gaacaggaaa    7560
gagaggaaca gggtcacaag gtgaaacctt aggagaaaag tggaaaaaga aattaaatca    7620
gttatcccgg aaagagtttg acctttacaa gaaatccgga atcaccgaag tggatagaac    7680
agaagccaaa gaagggttaa aaagaggaga ataacacac catgccgtgt ccagaggcag     7740
cgcaaaactt caatggttcg tggagagaaa catggtcatt cctgaaggaa gagtcataga    7800
cctaggctgt ggaagaggag gctggtcata ttactgtgca ggactgaaaa aagttacaga    7860
agtgcgagga tacacaaaag gcggcccagg acacgaagaa ccagtaccta tgtctacata    7920
cggatggaac atagtcaagt taatgagtgg aaaggatgtt ttttatctgc cacctgaaaa    7980
gtgtgatacc ctattgtgtg acattggaga atcttcacca agcccaacag tggaagaaag    8040
cagaaccata agagttttga agatggttga accatggcta agaacaaccc agttttgcat     8100
taaagtattg aacccataca tgccaactgt gattgagcac ttagaaagac tacaaggaa     8160
acatggagga atgcttgtga gaaatccact ctcacgaaac tccacgcacg aaatgtattg    8220
gatatccaat ggtacaggca atatcgtctc ttcagtcaac atggtatcca gattgctact    8280
gaacagattc acaatgacac acaggagacc caccatagaa aaagatgtgg atctaggagc    8340
aggaacccga catgtcaatg cggaaccaga aacacccaac atggatgtca ttggggaaag    8400
aataaaaagg atcaaagagg agcatagttc aacatggcac tatgatgatg aaaatccta    8460
caaaacgtgg gcttaccatg gatcctatga agtaaaagcc acaggctcag cctcctccat    8520
gataaatgga gtcgtgaaac tcctcacaaa accatgggat gtggtgccca tggtgacaca    8580
gatggcaatg acagatacaa ctccattcgg ccagcaaaga gttttaaag agaaagtgga     8640
caccaggaca cctaggccca tgccaggaac aagaaaggtt atggagatca cagcggagtg    8700
gctttggagg accctgggaa ggaacaaaag acccagatta tgcacaaggg aggaattcac    8760
aaagaaggtc agaaccaacg cagctatggg cgctgtcttc acagaagaga ccaatgggga    8820
cagtgcgaga gctgctgttg aggacgaaga attttggaaa cttgtggaca gagaacgtga    8880
actccacaaa ctgggcaagt gtggaagctg cgtttacaac atgatgggca agagagaaa    8940
aaaacttgga gagtttggta aagcaaaagg cagtagggct atatggtaca tgtggttggg    9000
agccaggtac cttgagttcg aggcgctcgg attcctcaat gaagaccact ggttctcgcg    9060
tgaaaactct tacagtggag tagaaggaga aggactgcac aagctgggat acatcttgag    9120
agatatttcc aagataccg gaggagccat gtatgctgat gacacagccg gttgggacac    9180
aagaataaca gaagatgacc tgcacaatga ggaaaaaatc acacagcaga tggacctga    9240
acacaggcag ctagcgaacg ctatattcaa gctcacatac caaaacaaag tggtcaaagt    9300
ccaacgacca actccaaagg gcacggtaat ggacatcata tctaggaaag accaaagagg    9360
cagtggacag gtgggaactt atggtctgaa cacattcacc aacatggaag cccagctaat    9420
cagacaaatg gaaggagaag gcgtgttgtc aaaggcagac tcgagaaccc ccatccgct    9480
agagaagaaa attacacaat ggttggaaac taaggagtg gaaaggttaa aagaatggc     9540
catcagcggg gatgattgcg ttgtgaaacc aatcgacgac agattcgcca atgccctgct    9600
tgccctgaac gatatgggaa aggttagaaa ggacatacct caatggcagc catcaaaggg    9660
```

-continued

```
atggcatgat tggcaacagg tccccttctg ctcccaccac tttcatgaat tgatcatgaa 9720
agatggaaga aagttggtag ttccctgcag accccaggac gaactaatag gaagagcgag 9780
aatctcccaa ggagcaggat ggagccttag agaaactgca tgtctaggga aagcctacgc 9840
tcaaatgtgg gctctcatgt attttcacag aagagatctt agactagcat ccaacgccat 9900
atgttcagca gtaccagtcc actgggtccc cacgagcaga acgacatggt ctattcatgc 9960
tcaccatcag tggatgacta cagaagacat gcttactgtc tggaacaggg tgtggataga 10020
ggacaatcca tggatggaag acaaaactcc agtcacaacg tgggaagatg ttccatatct 10080
agggaagaga gaagaccaat ggtgcggatc actcataggt ctcacttcca gagcaacctg 10140
ggcccagaac atactcacag caatccaaca ggtgagaagc ctcataggca atgaagagtt 10200
tctggactac atgccttcga tgaagagatt caggaaggag gaggagtcag agggagccat 10260
ttggtaaaag caggaggtaa actgtcaggc cacattaagc cacagtacgg aagaagctgt 10320
gcagcctgtg agccccgtcc aaggacgtta aaagaagaag tcaggcccaa aagccacggt 10380
ttgagcaaac cgtgctgcct gtagctccgt cgtggggacg taaagcctgg gaggctgcaa 10440
accgtggaag ctgtacgcac ggtgtagcag actagtggtt agaggagacc cctcccatga 10500
cacaacgcag cagcggggcc cgagcactga gggaagctgt acctccttgc aaaggactag 10560
aggttagagg agaccccccg caaacaaaaa cagcatattg acgctgggag agaccagaga 10620
tcctgctgtc tcctcagcat cattccaggc acagaacgcc agaaaatgga atggtgctgt 10680
tgaatcaaca ggttctagt 10699
```

<210> SEQ ID NO 12
<211> LENGTH: 10648
<212> TYPE: DNA
<213> ORGANISM: Dengue virus type 4 (LAV4)

<400> SEQUENCE: 12

```
agttgttagt ctgtgtggac cgacaaggac agttccaaat cggaagcttg cttaacacag 60
ttctaacagt ttgtttgaat agagagcaga tctctggaaa aatgaaccaa cgaaaaaagg 120
tggttagacc acctttcaat atgctgaaac gcgagagaaa ccgcgtatca acccctcaag 180
ggttggtgaa gagattctca accggacttt tttctgggaa aggaccctta cggatggtgc 240
tagcattcat cacgtttttg cgagtccttt ccatccccacc aacagcaggg attctgaaaa 300
gatggggaca gttgaagaaa aataaggcca tcaggatact gattggattc aggaaggaga 360
taggccgcat gctgaacatc ttgaacggga gaaaaaggtc aacgataaca ttgctgtgct 420
tgattcccac cgtaatggcg tttcacttgt caacaagaga tggcgaaccc ctcatgatag 480
tggcaaaaca tgaaaggggg agacctctct tgtttaagac aacagagggg atcaacaaat 540
gcactctcat tgccatggac ttgggtgaaa tgtgtgagga cactgtcacg tataaatgcc 600
ccttactggt caataccgaa cctgaagaca ttgattgctg gtgcaatctc acgtctacct 660
gggtcatgta tgggacatgc acccagagcg gagaacggag acgagagaag cgctcagtag 720
ctttaacacc acattcagga atgggattgg aaacaagagc tgagacatgg atgtcatcgg 780
aaggggcttg gaagcatgct cagagagtag agagctggat actcagaaac ccaggattcg 840
cgctcttggc aggatttatg gcttatatga ttgggcaaac aggaatccag cgaactgtct 900
tctttgtcct aatgatgctg gtcgccccat cctacggaat gcgatgcgta ggagtaggaa 960
acagagactt tgtggaagga gtctcaggtg gagcatgggt cgatctggtg ctagaacatg 1020
gaggatgcgt cacaaccatg gcccagggaa aaccaacctt ggattttgaa ctgactaaga 1080
```

```
caacagccaa ggaagtggct ctgttaagaa cctattgcat tgaagcctca atatcaaaca   1140
taaccacggc aacaagatgt ccaacgcaag gagagcctta tctaaaagag gaacaagacc   1200
aacagtacat ctgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccacgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggcttg   1560
tgcataagca atggtttttg gatctacctc taccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatctcaag tgcaaagtcc   1800
gtatggagaa attgagaatc aagggaatgt catacacgat gtgttcagga agttctcaa   1860 ttgacaaaga gatggcagaa acacagcatg ggacaacagt ggtgaaagtc aagtatgaag   1920
gtgctggagc tccgtgtaaa gtccccatag agataagaga tgtgaacaag aaaaaagtgg   1980
ttgggcgtat catctcatcc accccttggg ctgagaatac caacagtgca accaacatag   2040
agttagaacc cccctttggg gacagctaca tagtgatagg tgttggaaac agtgcattaa   2100
cactccattg gttcaggaaa gggagttcca ttggcaagat gtttgagtcc atatacagag   2160
gtgcaaaacg aatggccatt ctaggtgaaa cagcttggga ttttggttcc gttggtggac   2220
tgttcacatc attgggaaag gctgtgcacc aggttttttgg aagtgtgtat acaaccatgt   2280
ttggaggagt ctcatggatg attagaatcc taattgggtt cctagtgttg tggattggca   2340
cgaactcaag gaacacttca atggctatga cgtgcatagc tgttggagga atcactctgt   2400
ttctgggctt cacagttcaa gcagacatgg gttgtgtggt gtcatggagt gggaaagaat   2460
tgaagtgtgg aagcggaatt tttgtggttg acaacgtgca cacttggaca gaacagtaca   2520
aatttcaacc ggagtcccca gcgagactag cgtctgcaat attgaatgcc cacaaagatg   2580
gggtctgtgg aattagatca accacgagg ctggaaaatgt catgtggaag caaataacca   2640
acgagctaaa ttatgttctc tgggaaggag gacatgacct cactgtagtg ctggggatg   2700 tgaaggggt gttgaccaaa ggcaagagag cactcacacc cccagtgaat gatctgaaat   2760
attcatggaa gacatgggga aaagcaaaaa tcttcacccc agaagcaaga aatagcacat   2820
ttttaataga cggaccagac acctccgaat gccccaatga acgaagagca tggaactttc   2880
ttgaggtgga agactatgga tttggcatgt tcacgaccaa catatggatg aaattccgag   2940
aaggaagttc agaagtgtgt gaccacaggt taatgtcagc ggcaattaaa gatcagaaag   3000
ctgtgcatgc tgacatgggt tattggatag agagctcaaa aaaccagacc tggcagatag   3060
agaaagcatc tcttattgaa gtgaaaacat gtctctgtgcc caagaccac acattgtgga   3120 gcaatggagt gctggaaagc cagatgctca ttccaaaatc atatgcgggc cctttttcac   3180
accacaatta ccgccagggc tatgccacgc aaaccgtggg cccatggcac ttaggcaaat   3240
tagagataga ctttggagaa tgccccggaa caacagtcgc aattcaggag gattgtgacc   3300
atagaggccc atctttgagg accaccactg catctggaaa actagtcacg caatggtgct   3360
gccgctcctg cacgatgcct ccccttaaggt tcttgggaga agatgggtgc tggtatggga   3420
tggagattag gcccttgagt gaaaaagaag agaacatggt caaatcacag gtaacggccg   3480
```

```
gacagggcac atcagaaact ttttctatgg gtctgttgtg cctgaccttg tttgtggaag    3540
aatgcttgag gagaagagtc actaggaaac acatgatatt ggttgtggtg atcactcttt    3600
gtgccatcat cctaggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt ttttaaggaa actcacttca agagagacag    3780
cactaatggt aataggaatg gccatgacaa cggtgctttc aattccacat gaccttatgg    3840
aactcattga tggaatatca ctggggctaa ttttgctaaa aatagtgaca cattttgaca    3900
acacccaagt gggaacctta gcccttttcct tgaccttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctcttttaa    4200
agaatgatgt ccctttagct ggcccaatgg tggcaggagg cttacttctg gcggcttacg    4260
tgatgagtgg tagctcagca gatctgtcac tagagaaggc cgccaatgtg cagtgggatg    4320
aaatggcaga cataacaggc tcaagcccaa tcatagaagt gaagcaggat gaagatggct    4380 cttctctccat acgggacgtc gaggaaacca atatgataac ccttttggtg aaactggcac    4440
tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
ctcaaaaagc cgcactgtct gaaggagtgt acaggatcat gcaaagaggg ttatttggga    4620
aaactcaggt tggagtaggg atacacatgg aaggtgtatt tcacacaatg tggcatgtaa    4680
caagaggatc agtgatctgc catgagactg ggagattgga gccatcttgg gctgacgtca    4740
ggaatgacat gatatcatac ggtggggat ggagacttgg agacaaatgg gacaaagaag    4800
aagatgttca ggtcctcgcc atagaaccag gaaaaaatcc taaacatgtc caaacgaaac    4860
ccggcctttt caagacccta actggagaaa ttggagcagt aacattagat ttcaaacccg    4920
gaacgtctgg ttctcccatc atcaacagga aggaaaagt catcggactc tatggaaatg    4980
gagtagttac caaatcaggt gattacgtca gtgccataac gcaagccgaa agaattggag    5040
agccagatta tgaagtggat gaggacattt ttcgaaagaa aagattaact ataatggact    5100
tacaccccgg agctgaaaag acaaaaagaa ttcttccatc aatagtgaga gaagccttaa    5160
aaaggaggct gcgaaccttg attttggctc ccacgagagt ggtggcggcc gagatggaag    5220
aggccctacg tggactgcca atccgttatc agacccagc tgtgaaatca gaacacacag    5280
gaagagagat tgtagacctc atgtgtcatg caaccttcac aacaagactt ttgtcatcaa    5340
ccagagttcc aaattacaac ctcatagtga tggatgaagc acatttcacc gatcctctcta    5400 gtgtcgcggc tagaggatac atctcgacca gggtggaaat gggagaggca gcagccatct    5460
tcatgaccgc aaccctcccc ggagcgcacag atcccttttcc ccagagcaac agcccaatag    5520
aagacatcga gagggaaatt ccggaaaggt catggaacac agggttcgac tggataacag    5580
actaccaagg gaaaactgtg tggtttgttc ccagcataaa agctggaaat gacattgcaa    5640
attgtttgag aaagtcggga aagaaagtta tccagttgag taggaaaacc tttgatacag    5700
agtatccaaa aacgaaactc acggactggg attttgtggt cactacagac atatctgaaa    5760
tgggggccaa ttttagagct gggagagtga tagaccctag gagatgcctc aagccagtta    5820
tcctaacaga tgggccagag agagtcattt tagcaggtcc tattccagtg actccagcaa    5880
```

```
gcgctgctca gagaagaggg cgaataggaa ggaacccagc acaagaagac gaccaatacg   5940
ttttctccgg agacccacta aaaatgatg aagatcatgc ccactggaca gaagcaaaga    6000
tgctgcttga caatatctac accccagaag ggatcattcc aacattgttt ggtccggaaa   6060
gggaaaaaac ccaagccatt gatggagagt tcgcctcag aggggaacaa aggaagactt    6120
ttgtggaatt aatgaggaga ggagaccttc cggtgtggct gagctataag gtagcttctg   6180
ctggcatttc ttacaaagat cgggaatggt gcttcacagg ggaaaggaat aaccaaattt   6240
tagaagaaaa catggaggtt gaaatttgga ctagagaggg agaaaagaaa aagctaaggc   6300
caagatggtt agatgcacgt gtatacgctg accccatggc tttgaaggat tttaaggagt   6360
ttgctagtgg aaggaagagc ataactctcg acatcctaac agagattgcc agtttgccaa   6420
cttacctttc ctctagggcc aagctcgccc ttgataacat agtcatgctc cacacaacag   6480
aaagaggagg gagggcctac caacacgccc tgaacgaact cccggagtca ctggaaacac   6540
ttatgcttgt agctttacta ggtgctatga cagcaggtat cttcctgttt ttcatgcaag   6600
ggaaaggaat agggaaattg tcaatggggtt tgataaccat tgcggtggct agtggcttgt   6660
tctgggtagc agaaattcaa ccccagtgga tagcggcctc aatcatacta gagtttttttc   6720 tcatggtact gttgataccg gaaccagaaa acaaaggac cccacaagac aatcaattga    6780
tctacgtcat attgaccatt ctcaccatta ttggtctcat agcagccaac gagatggggc   6840
tgattgaaaa acaaaaacg attttgggt tttaccaggt aaaaacagaa accaccatcc     6900
tcgatgtgga cttgagacca gcttcagcat ggacgctcta tgcagtagcc accacawttc   6960
tgactcccat gctgagacac accatagaaa acacgtcggc caacctatct ctagcagcca   7020
ttgccaacca gcggccgtc ctaatggggc ttggaaaagg atggccgctc cacagaatgg    7080
acctcggtgt gccgctgtta gcaatgggat gctattctca agtgaaccca acaactttga   7140
cagcatcctt agtcatgctt tcagtccatt atgcaataat aggtccagga ttgcaggcaa   7200
aagccacaag agaggcccag aaaaggacag ctgctgggat catgaaaaac cccacggtgg   7260
acgggataac agtaatagat ctagaaccaa tatcctatga cccaaaattt gaaaagcaat   7320
tagggcaggt catgctactc gtcttgtgtg ctggacaact actcttgatg agaacaacat   7380
gggctttctg tgaagtcttg acttttggcca caggaccaat cttgaccttg tgggagggca   7440
acccgggaag gttttggaac acgaccatag ccgtatccac cgccaacatt ttcagggaa    7500 gttacctggc gggagctgga ctggcttttt cactcataaa gaatgycaca acccctagga   7560
ggggaactgg gaccacagga gagacactgg gagagaagtg aagagacag ctaaactcat    7620 takacagaaa agagtttgaa gagtataaaa gaagtggaat actagaagtg gacaggactg   7680
aagccaagtc tgccctgaaa gatgggtcta aaatcaagca tgcagtatct agagggtcca   7740
gtaagattag atggattgtt gagagaggga tggtaaagcc aaaagggaaa gttgtagatc   7800
ttggctgtgg gagaggagga tggtcttatt acatggcgac gctcaagaac gtgactgaag   7860
tgaaagggta tacaaaagga ggtccaggac atgaagaacc gattcccatg gctacttatg   7920
gctggaattt ggtcaaactc cattcagggg ttgacgtgtt ctacaaaccc acagagcaag   7980
tggacaccct gctctgtgat attggggagt catcttctaa tccaacaata gaggaaggaa   8040
gaacattaag agttttgaag atggtggagc catggctctc ttcaaaacct gaattctgca   8100
tcaaagtcct taaccctac atgccaacag tcatagaaga gctggagaaa ctgcagagaa    8160
aacatggtgg gaaccttgtc agatgccgc tgtccaggac ctccacccat gagatgtatt   8220
gggtgtcagg agcgtcggga aacattgtga gctctgtgaa cacaacatca aagatgttgt   8280
```

```
tgaacaggtt cacaacaagg cataggaaac ccacttatga aaggacgta gatcttgggg    8340 caggaacgag aagtgtctcc actgaaacag aaaaaccaga catgacaatt attgggagaa    8400
ggcttcagcg attgcaagag gagcacaaag aaacctggca ttatgatcag gaaaacccat    8460
acagaacctg ggcgtatcat ggaagctatg aagctccttc gacaggctct gcatcctcca    8520
tggtgaacgg ggtagtaaaa ctgctaacaa aaccttggga tgtggttcca atggtgaccc    8580
agttagccat gacagacaca acccctttg ggcaacaaag agtgttcaaa gagaaggtgg    8640
ataccagaac accacaacca aaacccggta cacgaatggt tatgaccacg acagccaatt    8700
ggctgtgggc cctccttggg aagaagaaaa atcccagact gtgcacaagg gaagagttca    8760
tctcaaaagt tagatcaaac gcagccatag gcgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctacaa catgatggga aaacgtgaga    8940
aaaagttagg agagtttggc agagccaagg gaagccgagc aatctggtac atgtggctgg    9000
gagcgcggtt tctggaattt gaagccctgg gttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aagaactgat cacggaacag atggcccccc    9240
accacaagat cctagccaaa gccattttca aactaaccta tcaaaacaaa gtggtgaaag    9300
tcctcagacc cacaccgaga ggagcggtga tggatatcat atccaggaaa gaccaaagag    9360
gtagtggaca agttggaaca tatggtttga acacattcac caacatggaa gttcaactca    9420
tccgccaaat ggaagctgaa ggagtcatca cacaagatga catgcagaac ccaaaagggt    9480
tgaaagaaag agttgagaaa tggctgaaag agtgtggtgt cgacaggtta aagaggatgg    9540
caatcagtgg agacgattgc gtggtgaagc ccctggatga gaggtttggc acttccctcc    9600
tcttcttgaa cgacatggga aaggtgagga aagacattcc gcagtgggaa ccatctaagg    9660
gatgaaaaaa ctggcaagag gttccttttt gctcccacca ctttcacaag atcttcatga    9720
aggatggccg ctcactagtt gttccatgta gaaaccagga tgaactgata gggagagcca    9780
gaatctcgca gggggctgga tggagcttaa gagaaacagc ctgcctgggc aaagcttacg    9840
cccagatgtg gtcgctcatg tacttccaca gaagggatct gcgtttagcc tccatggcca    9900
tatgctcagc agttccaacg gaatggtttc aacaagcag aacaaatgg tcaatccacg    9960 ctcatcatca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg acttctcc agagccacct     10140 gggcgaagaa cattcacacg gccataaccc aggtcagaaa cctgatcgga aaagaggaat   10200
acgtggatta catgccagta atgaaaagat acagcgctcc ttcagagagt gaaggagttc   10260
tgtaattacc aacaacaaac accaaaggct attgaagtca ggccacttgt gccacggctt   10320
gagcaaaccg tgctgcctgt agctccgcca ataatgggag gcgtgaaatc cctagggagg   10380
ccatgcgcca cggaagctgt acgcgtggca tattggacta gcggttagag gagaccctc    10440 ccatcactga caaaacgcag caaagggggg cccgaagcca ggaggaagct gtactcctgg   10500
tggaaggact agaggttaga ggagacccc ccaacacaaa aacagcatat tgacgctggg    10560
aaagaccaga gatcctgctg tctctgcaac atcaatccag gcacagagcg aagcaagatg   10620
gattggtgtt gttgatccaa caggttct                                     10648
```

<210> SEQ ID NO 13
<211> LENGTH: 10735
<212> TYPE: DNA
<213> ORGANISM: Dengue virus VDV1

<400> SEQUENCE: 13
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgagggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgcccccg 600
gatcactgag gcggaaccag atgacgttga ctgttggtgc aatgccacgg acacatgggt 660
gacctatgga acgtgctctc aaactggcga acaccgacga gacaaacgtt ccgtcgcatt 720
ggccccacac gtggggcttg gcctagaaac aagagccgaa acgtggatgt cctctgaagg 780
tgcttggaaa cagatacaaa aagtagagac ttgggctctg agacatccag gattcacggt 840
gatagccctt tttctagcac atgccatagg aacatccatc acccagaaag ggatcatttt 900
cattttgctg atgctggtaa caccatctat ggccatgcga tgcgtgggaa taggcaacag 960
agacttcgtg gaaggactgt caggagcaac atgggtggat gtggtactgg agcatggaag 1020
ttgcgtcacc accatggcaa aaaacaaacc aacactggac attgaactct tgaagacgga 1080
ggtcacaaac cctgcagttc tgcgtaaatt gtgcattgaa gctaaaatat caaacaccac 1140
caccgattcg agatgtccaa cacaaggaga agccacactg gtggaagaac aagacgcgaa 1200
ctttgtgtgc cgacgaacgt tcgtggacag aggctggggc aatggctgtg ggctattcgg 1260
aaaaggtagt ctaataacgt gtgccaagtt taagtgtgtg acaaaactag aaggaaagat 1320
agctcaatat gaaaacctaa aatattcagt gatagtcacc gtccacactg gagatcagca 1380
ccaggtggga aatgagacta cagaacatgg aacaactgca accataacac ctcaagctcc 1440
tacgtcggaa atacagctga ccgactacgg aacccttaca ttagattgtt cacctaggac 1500
agggctagat tttaacgaga tggtgttgct gacaatgaaa aagaaatcat ggcttgtcca 1560
caaacagtgg tttctagact taccactgcc ttggacctct ggggctttaa catcccaaga 1620
gacttggaac agacaagatt tactggtcac atttaagaca gctcatgcaa agaagcagga 1680
agtagtcgta ctaggatcac aagaaggagc aatgcacact gcgctgactg gagcgacaga 1740
aatccaaacg tcaggaacga caacaatttt cgcaggacac ctaaaatgca gactaaaaat 1800
ggacaaacta actttaaaag ggatgtcata tgtgatgtgc acaggctcat tcaagttaga 1860
gaaagaagtg gctgagaccc agcatggaac tgttctggtg caggttaaat atgaaggaac 1920
agacgcacca tgcaagattc ccttttcgac ccaagatgag aaaggagcaa cccagaatgg 1980
gagattaata acagccaacc ccatagtcac tgacaaagaa aaaccagtca atattgaggc 2040
agaaccaccc tttggtgaga gctacatcgt ggtaggagca ggtgaaaaag ctttgaaact 2100
aagctggttc aagaaaggaa gcagcatagg gaaaatgttt gaagcaactg cccgaggagc 2160

```
acgaaggatg gccattctgg gagacaccgc atgggacttc ggttctatag gaggagtgtt    2220
cacgtctatg ggaaaactgg tacaccaggt ttttggaact gcatatggag ttttgtttag    2280
cggagtttct tggaccatga aaataggaat agggattctg ctgacatggc taggattaaa    2340
ttcaaggaac acgtcccttt cggtgatgtg catcgcagtt ggcatggtca cactgtacct    2400
aggagtcatg gttcaggcag attcgggatg tgtaatcaac tggaaaggca gagaacttaa    2460
atgtggaagc ggcattttg tcactaatga agttcacact tggacagagc aatacaaatt     2520
ccaggctgac tcccccaaga gactatcagc agccattggg aaggcatggg aggagggtgt    2580
gtgtggaatc cgatcagcca ctcgtctcga aacatcatg tggaaacaaa tatcaaatga     2640
attgaaccac atcctacttg aaaatgacat gaaatttaca gtggtcgtgg agacgttag     2700 tggaatcttg gcccaaggra aaaaaatgat taggccacaa cccatggaac acaaatactc    2760
gtggaaaagc tggggaaaag ctaaaatcat aggagcggat gtacagaaca ccaccttcat    2820
catcgacggc ccaaacaccc cagaatgccc tgacaatcaa agagcatgga atatttggga    2880
agtagaggac tatggatttg gattttcac gacaaacata tggttgaaat tgcgtgactc     2940
ctacacccaa gtatgtgacc accggctgat gtcagctgcc attaaggaca gcaaggcagt    3000
ccatgctgac atggggtact ggatagaaag tgaaagaac gagacatgga agttggcgag     3060
agcctccttt atagaagtta agacatgcat ctggccaaaa tcccacactc tatggagcaa    3120
tggagttctg gaaagtgaaa tgataattcc aaagatatat ggaggaccaa tatctcagca    3180
caactacaga ccaggatatt tcacacaaac agcagggcg tggcacctag caagttgga      3240 actagatttc gattttgtg aaggtaccac agttgttgtg gatgaacatt gtggaaatcg      3300
aggaccatct ctcagaacca caacagtcac aggaaagata atccatgaat ggtgctgcag    3360
atcttgtacg ctaccccccc tacgtttcaa aggggaagac gggtgttggt acggcatgga    3420
aatcagacca gtgaaggaca aggaagagaa cctggtcaag tcaatggtct ctgcagggtc    3480
aggagaagtg gacagctttt cactaggact gctatgcata tcaataatga ttgaagaagt    3540
gatgagatcc agatggagca aaaaaatgct gatgactgga acactggctg tgttcctcct    3600
tcttataatg ggacaattga catggagtga tctgatcagg ttatgtatta tggttggagc    3660
caacgcttca gacaagatgg ggatgggaac aacgtaccta gctttaatgg ccactttcaa    3720
aatgagacca atgttcgccg tcgggctatt atttcgcaga ctaacatcta gagaagttct    3780
tcttcttaca attggcttga gcctggtggc atccgtggag ctaccaagtt ccctagagga    3840
gctgggggat ggacttgcaa taggcatcat gatgttgaaa ttattgactg attttcagtc    3900
acaccagcta tgggctactc tgctatcctt gacatttatt aaaacaactt tttcattgca    3960
ctatgcatgg aagacaatgg ctatggtact gtcaattgta tctctcttcc ctttatgcct    4020
gtccacgacc tctcaaaaaa caacatggct tccggtgctg ttgggatctc ttggatgcaa    4080
accactaccc atgtttctta acagaaaaa caaaatctgg ggaaggaaga gttggcccct    4140
caatgaagga attatggctg ttggaatagt tagtattcta ctaagttcac tttaaaaaa      4200 tgatgtgccg ctagccggcc cattaatagc tggaggcatg ctaatagcat gttatgtcat    4260
atccggaagc tcagctgatt tatcactgga gaaagcggct gaggtctcct gggaggaaga   4320
agcagaacac tcaggcgcct cacacaacat actagtagag gttcaagatg atggaaccat    4380
gaagataaaa gatgaagaga gagatgacac gctcaccatt ctccttaaag caactctgct    4440
ggcagtctca ggggtgtacc caatgtcaat accagcgacc cttttgtgt ggtatttttg      4500 gcagaaaaag aaacagagat caggagtgct atgggacaca cccagccccc cagaagtgga    4560
```

```
aagagcagtt cttgatgatg gcatctatag aattttgcaa agaggactgt tgggcaggtc    4620
ccaagtagga gtaggagttt tccaagaagg cgtgttccac acaatgtggc acgtcactag    4680
gggagctgtc ctcatgtatc aaggaaaaag gctggaacca agctgggcca gtgtcaaaaa    4740
agacttgatc tcatatggag gaggttggag gtttcaagga tcctggaaca cgggagaaga    4800
agtacaggtg attgctgttg aaccgggaaa aaaccccaaa aatgtacaaa caacgccggg    4860
taccttcaag accccctgaag gcgaagttgg agccatagcc ttagacttta aacctggcac    4920
atctggatct cccatcgtaa acagagaggg aaaaatagta ggtctttatg gaaatggagt    4980
ggtgacaaca agcggaactt acgttagtgc catagctcaa gctaaggcat cacaagaagg    5040
gcctctacca gagattgagg acaaggtgtt taggaaaaga aacttaacaa taatggacct    5100
acatccagga tcgggaaaaa caagaagata ccttccagcc atagtccgtg aggccataaa    5160
aaggaagctg cgcacgctaa tcctagctcc cacaagagtt gtcgcttctg aaatggcaga    5220
ggcactcaag ggagtgccaa taaggtatca gacaacagca gtgaagagtg aacacacagg    5280
aaaggagata gttgacctta tgtgccacgc cactttcacc atgcgcctcc tgtctcccgt    5340
gagagttccc aattataaca tgattatcat ggatgaagca cacttcaccg atccagccag    5400
catagcagcc agagggtaca tctcaacccg agtgggtatg ggtgaagcag ctgcgatctt    5460
tatgacagcc actcccccag gatcggtgga ggcctttcca cagagcaatg caattatcca    5520
agatgaggaa agagacattc ctgagagatc atggaactca ggctatgact ggatcactga    5580
ttttccaggt aaaacagtct ggtttgttcc aagcatcaaa tcaggaaatg acattgccaa    5640
ctgtttaaga aaaacggga acgggtgat ccaattgagc agaaaaacct tgacactga    5700 gtaccagaaa acaaaaaaca acgactggga ctatgtcgtc acaacagaca tttccgaaat    5760
gggagcaaat ttccgggccg acagggtaat agacccaagg cggtgtctga aaccggtaat    5820
actaaaagat ggtccagagc gcgtcattct agccggaccg atgccagtga ctgtggccag    5880
tgccgcccag aggagaggaa gaattggaag gaaccaaaac aaggaaggtg atcagtatat    5940
ttacatggga cagcctttaa aaatgatga ggaccacgct cattggacag aagcaaagat    6000
gctccttgac aatataaaca caccagaagg gattatccca gccctctttg agccggagag    6060
agaaaagagt gcagctatag acggggaata cagactgcgg ggtgaagcaa ggaaaacgtt    6120
cgtggagctc atgagaagag gggatctacc agtctggcta tcctacaaag ttgcctcaga    6180
aggcttccag tactccgaca gaaggtggtg cttcgatggg gaaaggaaca accaggtgtt    6240
ggaggagaac atggacgtgg agatctggac aaaagaagga gaaagaaaga aactacgacc    6300
tcgctggttg gacgccagaa catactctga cccactggct ctgcgcgagt ttaaagagtt    6360
tgcagcagga agaagaagcg tctcaggtga cctaatatta gaatagggaa acttccaca    6420 acatttgacg caagggccc agaatgcttt ggacaacttg gtcatgttgc acaattccga    6480
acaaggagga aaagcctata gacatgctat ggaagaactg ccagacacaa tagaaacgtt    6540
gatgctccta gccttgatag ctgtgttgac tggtggagtg acgctgttct tcctatcagg    6600
aagaggtcta ggaaaaacat ctatcggctt actctgcgtg atggcctcaa gcgcactgtt    6660
atggatggcc agtgtggagc cccattggat agcggcctcc atcatactgg agttctttct    6720
gatggtactg cttattccag agccagacag acagcgcact ccacaggaca accagctagc    6780
atatgtggtg ataggtctgt tattcgtgat attgacagtg gcagccaatg agatgggatt    6840
attggaaacc acaaagaaag acctggggat tggccatgta gctgctgaaa accaccacca    6900
tgctacaatg ctggacgtag acctacatcc agcttcagcc tggaccctct atgcagtggc    6960
```

```
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaggct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
attttgcata aaaattctaa atcctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca atggctcaca ggaagccaca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatgggaaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca acttggata   9120 catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
```

```
ccagagaggc agtggacagg ttggaactta tggcttaaac actttcacca acatggaggc    9420
ccaactgata agacaaatgg agtctgaggg aatcttttta cccagcgaat ggaaacccc     9480 aaatctagcc ggaagagttc tcgactggtt ggaaaaatat ggtgtcgaaa ggctgaaaag    9540
aatggcaatc agcggagatg actgtgtggt gaaaccaatt gatgacaggt tcgcaacagc    9600
cttaacagct ttgaatgaca tgggaaaagt aagaaaagac ataccacaat gggaaccttc    9660
aaaaggatgg aatgattggc aacaagtgcc tttctgttca caccacttcc accagctaat    9720
tatgaaggat gggagggaga tagtggtgcc atgccgcaac caagatgaac ttgtggggag    9780
ggccagagta tcacaaggcg ccggatggag cctgagagaa accgcatgcc taggcaagtc    9840
atatgcacaa atgtggcagc tgatgtattt ccacaggaga gacctgagac tggcggctaa    9900
cgctatttgt tcagccgttc cagttgattg ggtcccaacc agccgcacca cctggtcgat    9960
ccatgcccat caccaatgga tgacaacaga agacatgtta tcagtatgga atagggtctg    10020
gatagaggaa aacccatgga tggaggataa gactcatgtg tccagttggg aagaagttcc    10080
ataccaggca agagggaag atcagtggtg tggatcccgg ataggcttaa cagcaagggc    10140
cacctgggcc actaatatac aagtggccat aaaccaagtg agaaggctca ttgggaatga    10200
gaattatcta gattacatga catcaatgaa gagattcaag aatgagagtg atcccgaagg    10260
ggcactctgg taagtcaaca cattcacaaa ataaggaaa ataaaaaatc aaatgaggca    10320
agaagtcagg ccagattaag ccatagtacg gtaagagcta tgctgcctgt gagccccgtc    10380
caaggacgta aaatgaagtc aggccgaaag ccacggtttg agcaagccgt gctgcctgtg    10440
gctccatcgt ggggatgtaa aaacccggga ggctgcaacc catggaagct gtacgcatgg    10500
ggtagcagac tagtggttag aggagacccc tcccaagaca caacgcagca gcggggccca    10560
acaccagggg aagctgtacc ctggtggtaa ggactagagg ttagaggaga ccccccgcgt    10620
aacaataaac agcatattga cgctgggaga accagagat cctgctgtct ctacagcatc    10680
attccaggca cagaacgcca gaaaatggaa tggtgctgtt gaatcaacag gttct         10735
```

<210> SEQ ID NO 14
<211> LENGTH: 10723
<212> TYPE: DNA
<213> ORGANISM: Dengue virus VDV2
<220> FEATURE:
<221> NAME/KEY: misc_feature
<222> LOCATION: (10361)..(10361)
<223> OTHER INFORMATION: n is a, c, g, or t

<400> SEQUENCE: 14
agttgttagt ctacgtggac cgacaaagac agattctttg agggagctaa gctcaatgta 60
gttctaacag tttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggttggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660

```
gtaacttatg ggacgtgtac caccatggga gaacatagaa gagaaaaaag atcagtggca      720
ctcgttccac atgtgcgaat gggactggag acacgaactg aaacatggat gtcatcagaa      780
ggggcctgga acatgtcca gagaattgaa acttggatct tgagacatcc aggcttcacc       840
atgatggcag caatcctggc atacaccata ggaacgacac atttccaaag agccctgatt      900
ttcatcttac tgacagctgt cactccttca atgacaatgc gttgcatagg aatgtcaaat      960
agagactttg tggaaggggt ttcaggagga agctgggttg acatagtctt agaacatgga     1020
agctgtgtga cgacgatggc aaaaaacaaa ccaacattgg atttttgaact gataaaaaca     1080
gaagccaaac agcctgccac cctaaggaag tactgtatag aggcaaagct aaccaacaca     1140
acaacagaat ctcgctgccc aacacaaggg gaacccagcc taaatgaaga gcaggacaaa     1200
aggttcgtct gcaaacactc catggtagac agaggatggg gaaatggatg tggactattt     1260
ggaaagggag gcattgtgac ctgtgctatg ttcagatgca aaaagaacat ggaaggaaaa     1320
gttgtgcaac cagaaaactt ggaatacacc attgtgataa cacctcactc aggggaagag     1380
catgcagtcg gaaatgacac aggaaaacat ggcaaggaaa tcaaaataac accacagagt     1440
tccatcacag aagcagaatt gacaggttat ggcactgtca caatggagtg ctctccaaga     1500
acgggcctcg acttcaatga gatggtgttg ctgcagatgg aaaataaagc ttggctggtg     1560
cacaggcaat ggttcctaga cctgccgtta ccatggttgc ccggagcgga cacacaagag     1620
tcaaattgga tacagaarga gacattggtc actttcaaaa atccccatgc gaagaaacag     1680
gatgttgttg ttttaggatc ccaagaaggg gccatgcaca cagcacttac aggggccaca     1740
gaaatccaaa tgtcatcagg aaacttactc ttcacaggac atctcaagtg caggctgaga     1800
atggacaagc tacagctcaa aggaatgtca tactctatgt gcacaggaaa gtttaaagtt     1860
gtgaaggaaa tagcagaaac acaacatgga acaatagtta tcagagtgca atatgaaggg     1920
gacggctctc catgcaagat ccctttttgag ataatggatt tggaaaaaag acatgtctta     1980
ggtcgcctga ttacagtcaa cccaattgtg acagaaaaag atagcccagt caacatagaa     2040
gcagaacctc catttggaga cagctacatc atcataggag tagagccggg acaactgaag     2100
ctcaactggt ttaagaaagg aagttctatc ggccaaatgt ttgagacaac aatgaggggg     2160
gcgaagagaa tggccattt aggtgacaca gcctgggatt ttggatcctt gggaggagtg     2220
tttacatcta taggaaaggc tctccaccaa gtctttggag caatctatgg agctgccttc     2280
agtggggttt catggactat gaaaatcctc ataggagtca ttatcacatg gataggaatg     2340
aattcacgca gcacctcact gtctgtgaca ctagtattgg tgggaattgt gacactgtat     2400
ttgggagtca tggtgcaggc cgatagtggt tgcgttgtga ctggaaaaaa caaagaactg     2460
aaatgtggca gtgggatttt catcacagac aacgtgcaca catggacaga acaatacaar     2520
ttccaaccag aatccccttc aaaactagct tcagctatcc agaaagccca tgaagaggac     2580
atttgtggaa tccgctcagt aacaagactg gagaatctga tgtggaaaca aataacacca     2640
gaattgaatc acattctatc agaaaatgag gtgaagttaa ctattatgac aggagacatc     2700
aaaggaatca tgcaggcagg aaaacgatct ctgcggcctc agcccactga gctgaagtat     2760
tcatggaaaa catggggcaa agcaaaaatg ctctctacag agtctcataa ccagaccttt     2820
ctcattgatg gccccgaaac agcagaatgc cccaacacaa atagagcttg gaattcgttg     2880
gaagttgaag actatggctt tggagtattc accaccaata tatggctaaa attgaaagaa     2940
aaacaggatg tattctgcga ctcaaaactc atgtcagcgg ccataaaaga caacagagcc     3000
gtccatgccg atatgggtta ttggatagaa agtgcactca atgacacatg gaagatagag     3060
```

```
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
cacaactata gaccaggcta ccatacacaa ataacaggac catggcatct aggtaagctt    3240
gagatggact ttgatttctg tgatggaaca acagtggtag tgactgagga ctgcggaaat    3300
agaggaccct ctttgagaac aaccactgcc tctggaaaac tcataacaga atggtgctgc    3360
cgatcttgca cattaccacc gctaagatac agaggtgagg atgggtgctg gtacgggatg    3420
gaaatcagac cattgaagga gaaagaagag aatttggtca actccttggt cacagctgga    3480
catgggcagg tcgacaactt ttcactagga gtcttgggaa tggcattgtt cctggaggaa    3540
atgcttagga cccgagtagg aacgaaacat gcaatactac tagttgcagt ttcttttgtg    3600
acattgatca cagggaacat gtcctttaga gacctgggaa gagtgatggt tatggtaggc    3660
gccactatga cggatgacat aggtatgggc gtgacttatc ttgccctact agcagccttc    3720
aaagtcagac caacttttgc agctggacta ctcttgagaa agctgacctc caaggaattg    3780
atgatgacta ctataggaat tgtactcctc tcccagagca ccataccaga gaccattctt    3840
gagttgactg atgcgttagc cttaggcatg atggtcctca aaatggtgag aaatatggaa    3900
aagtatcaat tggcagtgac tatcatggct atcttgtgcg tcccaaacgc agtgatatta    3960
caaaacgcat ggaaagtgag ttgcacaata ttggcagtgg tgtccgtttc cccactgttc    4020
ttaacatcct cacagcaaaa aacagattgg ataccattag cattgacgat caaaggtctc    4080
aatccaacag ctattttctc taacaaccctc tcaagaacca gcaagaaaag gagctggcca    4140
ttaaatgagg ctatcatggc agtcgggatg gtgagcattt tagccagttc tctcctaaaa    4200
aatgatattc ccatgacagg accattagtg gctggagggc tcctcactgt gtgctacgtg    4260
ctcactggac gatcggccga tttggaactg gagagagcag ccgatgtcaa atgggaagac    4320
caggcagaga tatcaggaag cagtccaatc ctgtcaataa caatatcaga agatggtagc    4380
atgtcgataa aaaatgaaga ggaagaacaa acactgacca tactcattag aacaggattg    4440
ctggtgatct caggactttt tcctgtatca ataccaatca cggcagcagc atggtacctg    4500
tgggaagtga agaaacaacg ggccggagta ttgtgggatg ttccttcacc cccacccatg    4560
ggaaaggctg aactgaagga tggagcctat agaattaagc aaaaagggat tcttggatat    4620
tcccagatcg gagccggagt ttacaaagaa ggaacattcc atacaatgtg gcatgtcaca    4680
cgtggcgctg ttctaatgca taaaggaaag aggattgaac caacatgggc ggacgtcaag    4740
aaagacctaa tatcatatgg aggaggctgg aagttagaag gagaatggaa ggaaggagaa    4800
gaagtccagg tattggcact ggagcctgga aaaaatccaa gagccgtcca aacgaaacct    4860
ggtcttttca aaccaacgc cggaacaata ggtgctgtat ctctggactt ttctcctgga    4920
acgtcaggat ctccaattat cgacaaaaaa ggaaaagttg tgggtcttta tggtaatggt    4980
gttgttacaa ggagtggagc atatgtgagt gctatagccc agactgaaaa aagcattgaa    5040
gacaacccag agatcgaaga tcacattttc cgaaagagaa gactgaccat catggacctc    5100
cacccaggag cggaaagac gaagagatac cttccggcca tagtcagaga agctataaaa    5160
cggggtttga acattaat cttggccccc actagagttg tggcagctga aatggaggaa    5220
gcccttagag gacttccaat aagataccag accccagcca tcagctgaa gcacaccggg    5280 cgggagattg tggacctaat gtgtcatgcc acatttacca tgaggctgct atcaccagtt    5340
agagtgccaa actacaacct gattatcatg gacgaagccc atttcacaga cccagcaagt    5400
atagcagcta gaggatacat ctcaactcga gtggagatgg gtgaggcagc tgggattttt    5460
```

```
atgacagcca ctcccccggg aagcagagac ccatttcctc agagcaatgc accaatcata   5520
gatgaagaaa gagaaatccc tgaacgctcg tggaattccg acatgaatg ggtcacggat    5580 tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata daccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct ttttattctt gatgagcgca   6600 agggcatag gaagatgac cctgggaatg tgctgcataa tcacggctag catcctccta   6660
tggtacgcac aaatacagcc acactggata gcagcttcaa taatactgga gttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa agccgattg   7620 aacgcattgg gaaaagtga attccagatc tacaagaaaa gtggaatcca ggaagtggat   7680
agaaccttag caaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
```

```
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt ttttaaagag   8640
aaagtggaca cgaaaccca agaaccgaaa gaaggcacga agaaactaat gaaaataaca   8700
```

```
gttctgtggt agaaagcaaa actaacatga aacaaggcta gaagtcaggt cggattaagc    10320
catagtacgg aaaaaactat gctacctgtg agccccgtcc naggacgtta aaagaagtca    10380
ggccatcata aatgccatag cttgagtaaa ctatgcagcc tgtagctcca cctgagaagg    10440
tgtaaaaaat ccgggaggcc acaaaccatg gaagctgtac gcatggcgta gtggactagc    10500
ggttagggga gacccctccc ttacaaatcg cagcaacaat gggggcccaa ggcgagatga    10560
agctgtagtc tcgctggaag gactagaggt tagaggagac cccccgaaa caaaaaacag     10620 catattgacg ctgggaaaga ccagagatcc tgctgtctcc tcagcatcat tccaggcaca    10680
gaacgccaga aaatggaatg gtgctgttga atcaacaggt tct                      10723
```